United States Patent
Akasaka et al.

(10) Patent No.: US 11,885,763 B2
(45) Date of Patent: Jan. 30, 2024

(54) GAS CONCENTRATION MEASUREMENT SYSTEM AND GAS CONCENTRATION MEASUREMENT METHOD

(71) Applicant: ROHM Co., LTD., Kyoto (JP)

(72) Inventors: Shunsuke Akasaka, Kyoto (JP); Yurina Amamoto, Kyoto (JP); Ken Nakahara, Kyoto (JP)

(73) Assignee: ROHM Co., LTD., Kyoto (JP)

( * ) Notice: Subject to any disclaimer, the term of this patent is extended or adjusted under 35 U.S.C. 154(b) by 0 days.

(21) Appl. No.: 17/166,221

(22) Filed: Feb. 3, 2021

(65) Prior Publication Data

US 2021/0247352 A1 Aug. 12, 2021

(30) Foreign Application Priority Data

Feb. 10, 2020 (JP) .................. 2020-020269

(51) Int. Cl.
*G01N 27/406* (2006.01)
*G01N 27/407* (2006.01)
(Continued)

(52) U.S. Cl.
CPC ..... *G01N 27/4065* (2013.01); *G01N 27/4067* (2013.01); *G01N 27/4074* (2013.01); *G01N 27/419* (2013.01); *G01N 33/0037* (2013.01)

(58) Field of Classification Search
CPC ........... G01N 27/4065; G01N 27/4067; G01N 27/4074; G01N 27/419; G01N 33/0037; G01N 27/407; Y02A 50/20
See application file for complete search history.

(56) References Cited

U.S. PATENT DOCUMENTS 4,595,485 A * 6/1986 Takahashi .......... G01N 27/4065
204/192.15
6,007,697 A * 12/1999 Yagi .................. G01N 27/4065
205/788
(Continued)

FOREIGN PATENT DOCUMENTS

JP S6064243 A * 4/1985
JP S62150153 7/1987
(Continued)

OTHER PUBLICATIONS

Suzuki et al., English translation of JP2004205357A, 2004 (Year: 2004).*

(Continued)

*Primary Examiner* — Joshua L Allen
*Assistant Examiner* — Shizhi Qian
(74) *Attorney, Agent, or Firm* — CHIP LAW GROUP

(57) ABSTRACT

A gas concentration measurement system includes a limiting current-type gas sensor, a voltage source connected to the limiting current-type gas sensor, a current detector connected to the limiting current-type gas sensor, and a gas concentration arithmetic unit connected to the current detector. The voltage source supplies first and second voltages to the limiting current-type gas sensor. The first and second voltages generate first and second limiting currents corresponding to first and second gases, respectively, in the limiting current-type gas sensor. The current detector acquires first and second limiting current values of the limiting current-type gas sensor when the first and second voltages are applied to the limiting current-type gas sensor, respectively. The gas concentration arithmetic unit includes a difference acquiring section that acquires a difference between the second and first limiting current values and a (Continued)

gas concentration acquiring section that obtains concentration of the second gas based on the difference.

10 Claims, 8 Drawing Sheets

(51) Int. Cl.
    *G01N 33/00*     (2006.01)
    *G01N 27/419*     (2006.01)

(56) References Cited

U.S. PATENT DOCUMENTS

| | | | | |
|---|---|---|---|---|
| 2012/0217160 A1* | 8/2012 | Hayashi | ............ | G01N 27/4071 204/424 |
| 2017/0299543 A1* | 10/2017 | Akasaka | ............ | G01N 27/419 |
| 2018/0335400 A1* | 11/2018 | Mitsuno | ............ | G01N 27/4065 |

FOREIGN PATENT DOCUMENTS

| | | | | |
|---|---|---|---|---|
| JP | H01114745 A | * | 5/1989 | |
| JP | Hei 10-38845 | | 8/1999 | |
| JP | 2004205357 A | * | 7/2004 | |
| JP | 2010-048596 | | 3/2010 | |
| JP | 2015-212649 | | 11/2015 | |
| JP | 2016099317 A | * | 5/2016 | |
| JP | 2017190986 A | * | 10/2017 | |
| JP | 2018-132368 | | 8/2018 | |
| JP | 2019-086338 | | 6/2019 | |
| WO | WO-2019088026 A1 | * | 5/2019 | ......... F02D 41/1454 |

OTHER PUBLICATIONS

Haruki et al., English translation of WO-2019088026-A1, 2019 (Year: 2019).*
Notice of Reasons for Refusal cited in Japanese Application No. 2020020269, dated Oct. 24, 2023.

* cited by examiner

FIG.3
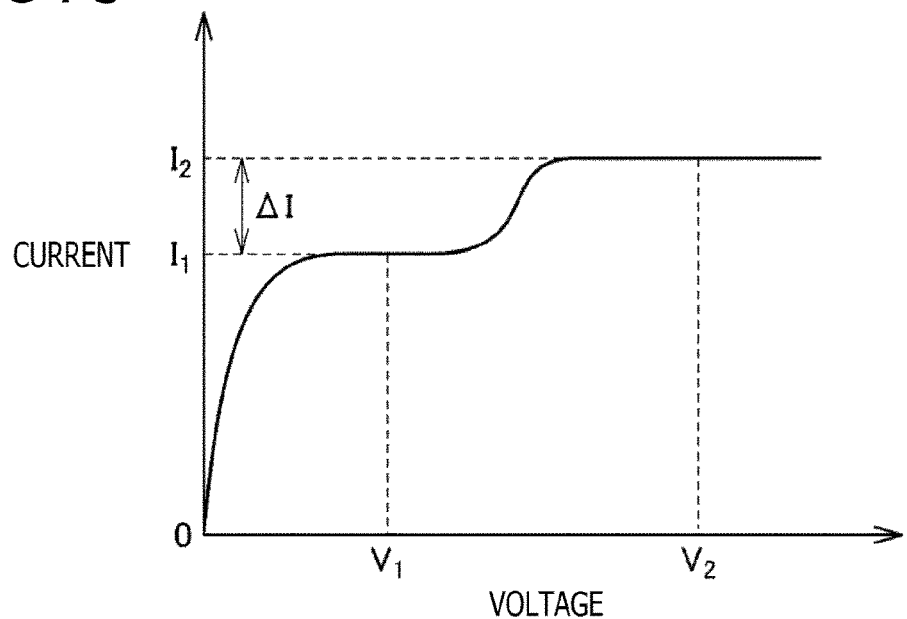
FIG.4
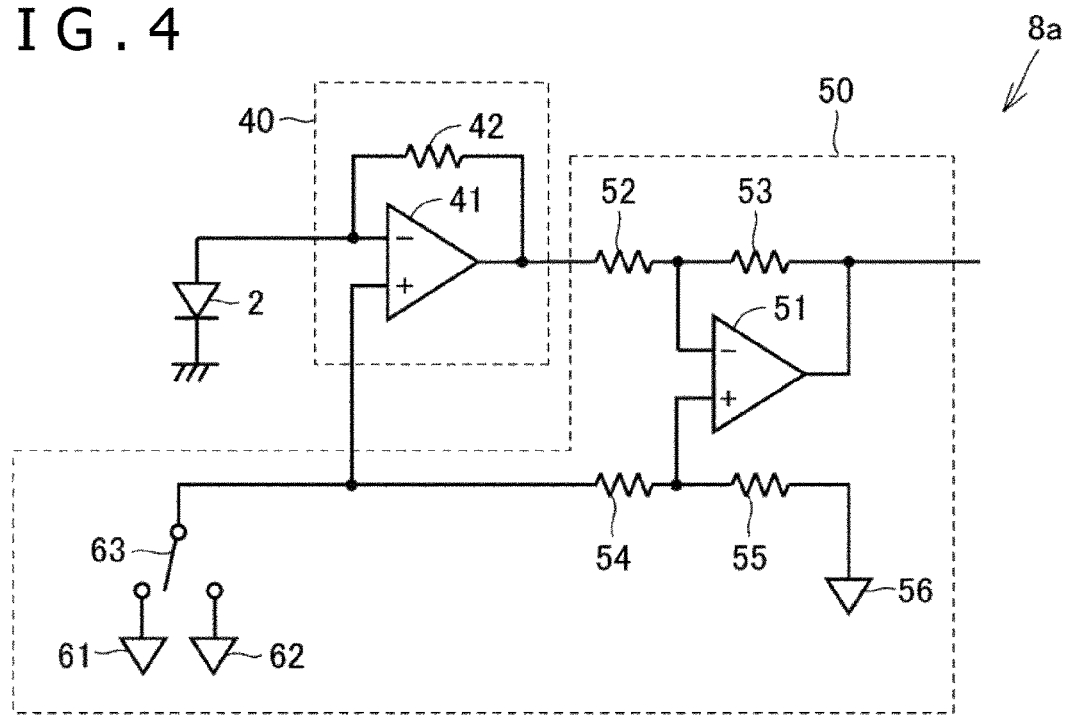
FIG.5

GAS CONCENTRATION MEASUREMENT SYSTEM AND GAS CONCENTRATION MEASUREMENT METHOD

CROSS REFERENCE TO RELATED APPLICATIONS

This application claims priority benefit of Japanese Patent Application No. JP 2020-020269 filed in the Japan Patent Office on Feb. 10, 2021. Each of the above-referenced applications is hereby incorporated herein by reference in its entirety.

BACKGROUND

The present disclosure relates to a gas concentration measurement system and a gas concentration measurement method.

Japanese Patent Laid-Open No. Hei 10-38845 (Patent Document 1) discloses a gas sensor that measures the concentration of nitrogen oxides ($NO_X$) in a measurement-target gas containing oxygen ($O_2$) and the nitrogen oxides ($NO_X$). Concretely, this gas sensor has a first chamber and a second chamber that communicates with the first chamber. In the first chamber, the oxygen contained in the measurement-target gas is removed to greatly lower the oxygen concentration in the measurement-target gas. The measurement-target gas with the greatly-lowered oxygen concentration flows to the second chamber. In the second chamber, the $NO_X$ contained in the measurement-target gas are decomposed into nitrogen ($N_2$) and oxygen ($O_2$). Oxygen ions obtained from the oxygen arising from the decomposition from the $NO_X$ are conducted in a solid electrolyte, and a limiting current flows in the solid electrolyte. The magnitude of this limiting current (limiting current value) is proportional to the amount of oxygen ions, i.e., the concentration of the $NO_X$. The concentration of the $NO_X$ contained in the measurement-target gas is obtained from the limiting current value.

SUMMARY

However, the gas sensor disclosed in Patent Document 1 has the first chamber and the second chamber, and therefore, the size of the gas sensor is large. The present disclosure is made in view of the above-described problem, and it is desirable to provide a gas concentration measurement system with a reduced size and a gas concentration measurement method that enables size reduction of a gas concentration measurement system.

A gas concentration measurement system according to an embodiment of the present disclosure includes a limiting current-type gas sensor, a voltage source connected to the limiting current-type gas sensor, a current detector connected to the limiting current-type gas sensor, and a gas concentration arithmetic unit connected to the current detector. The voltage source supplies a first voltage and a second voltage higher than the first voltage to the limiting current-type gas sensor. The first voltage is a voltage that generates a first limiting current corresponding to a first gas in the limiting current-type gas sensor. The second voltage is a voltage that generates a second limiting current corresponding to a second gas in the limiting current-type gas sensor. The current detector acquires a first limiting current value of the limiting current-type gas sensor when the first voltage is applied to the limiting current-type gas sensor and a second limiting current value of the limiting current-type gas sensor when the second voltage is applied to the limiting current-type gas sensor. The gas concentration arithmetic unit includes a difference acquiring section that acquires a difference between the second limiting current value and the first limiting current value and a gas concentration acquiring section that obtains concentration of the second gas on the basis of the difference.

A gas concentration measurement method according to an embodiment of the present disclosure includes applying a first voltage from a voltage source to a limiting current-type gas sensor and acquiring a first limiting current value of the limiting current-type gas sensor by using a current detector. The first voltage is a voltage that generates a first limiting current corresponding to a first gas in the limiting current-type gas sensor. The gas concentration measurement method according to the embodiment of the present disclosure includes applying a second voltage higher than the first voltage from the voltage source to the limiting current-type gas sensor and acquiring a second limiting current value of the limiting current-type gas sensor by using the current detector. The second voltage is a voltage that generates a second limiting current corresponding to a second gas in the limiting current-type gas sensor. The gas concentration measurement method according to the embodiment of the present disclosure includes acquiring a difference between the second limiting current value and the first limiting current value and obtaining concentration of the second gas on the basis of the difference.

According to the gas concentration measurement system of the present disclosure, the size of the gas concentration measurement system can be reduced. According to the gas concentration measurement method of the present disclosure, size reduction of the gas concentration measurement system is enabled.

BRIEF DESCRIPTION OF THE DRAWINGS

FIG. 3 is a diagram illustrating a current-voltage characteristic of the gas concentration measurement system (limiting current-type gas sensor element) of embodiment 1;

FIG. 4 is a diagram illustrating an electrical circuit of one example of a difference acquiring section of the gas concentration measurement system of embodiment 1;

FIG. 5 is a diagram illustrating one example of a data table stored in a memory of the gas concentration measurement system of embodiment 1;

DETAILED DESCRIPTION OF THE PREFERRED EMBODIMENTS

Figure 1:
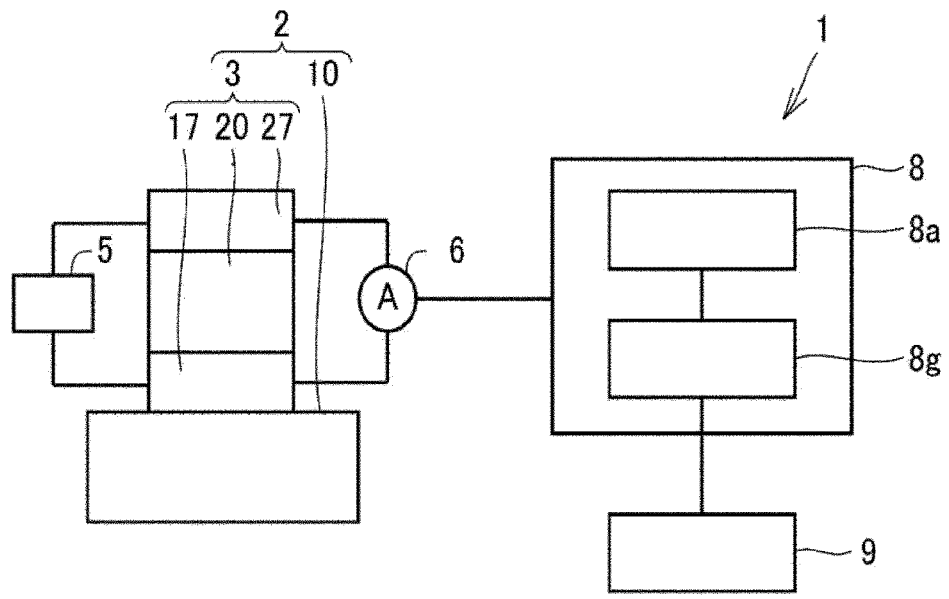
FIG. 1 is a schematic diagram of a gas concentration measurement system of embodiment 1.
Figure 2:
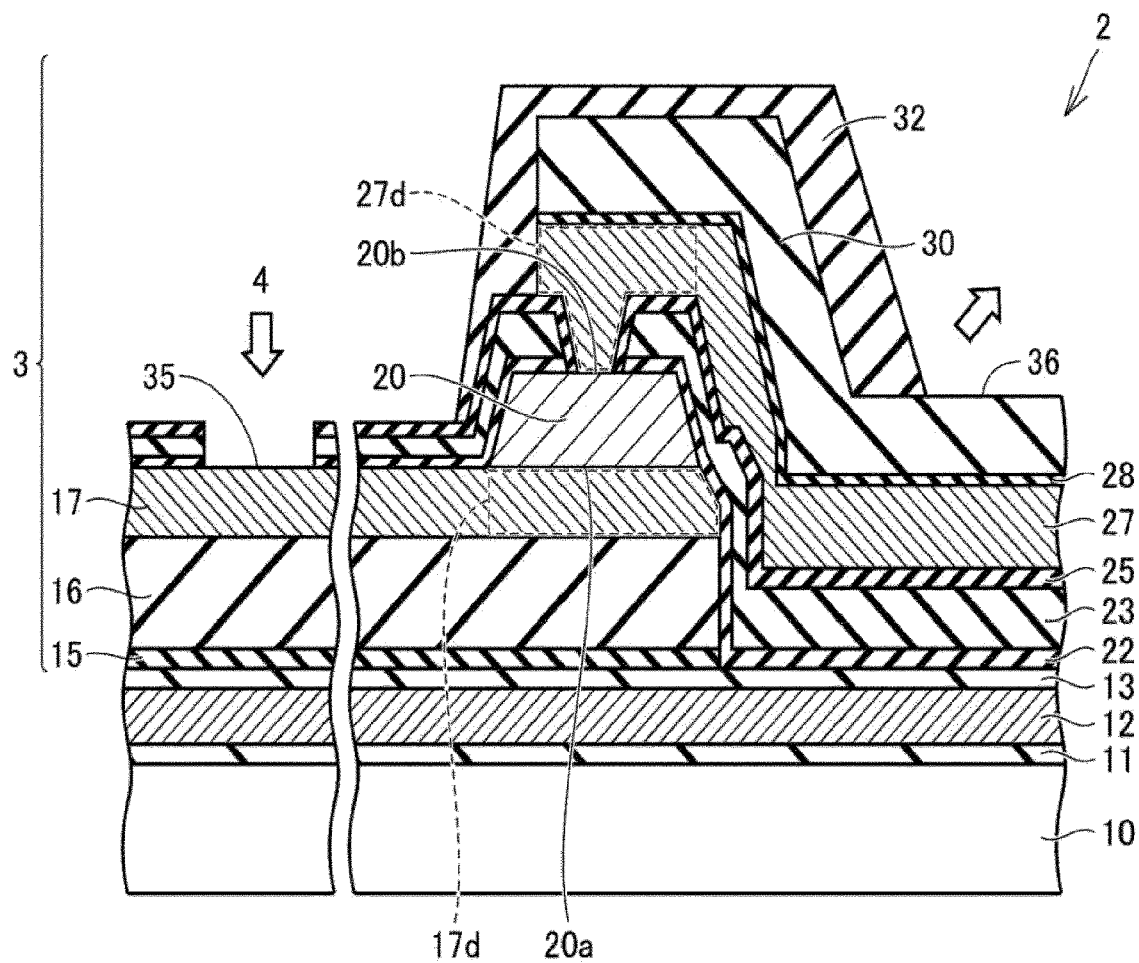
FIG. 2 is a schematic partially-enlarged sectional view illustrating one example of a limiting current-type gas sensor element of the gas concentration measurement system of embodiment 1.

Embodiments will be described below. The same configuration is given the same reference symbol and description thereof is not repeated.

Embodiment 1

A gas concentration measurement system 1 of embodiment 1 will be described with reference to FIG. 1 to FIG. 5. The gas concentration measurement system 1 can measure the concentration of a second gas in a measurement-target gas 4 containing a first gas and the second gas. The measurement-target gas 4 is the exhaust gas of an automobile, for example. The first gas is oxygen ($O_2$), for example. The second gas is nitrogen oxides ($NO_x$), for example.

The gas concentration measurement system 1 mainly includes a limiting current-type gas sensor 2, a voltage source 5, a current detector 6, a gas concentration arithmetic unit 8, and a memory 9.

The limiting current-type gas sensor 2 may be a thin-film limiting current-type gas sensor or may be a bulk limiting current-type gas sensor. The configuration of a thin-film limiting current-type gas sensor that is one example of the limiting current-type gas sensor 2 will be described with reference to FIG. 2.

The limiting current-type gas sensor 2 mainly includes a limiting current-type gas sensor element 3. The limiting current-type gas sensor 2 may further include a substrate 10, a heater 12, and insulating layers 11 and 13.

The substrate 10 is a silicon (Si) substrate but is not particularly limited thereto. The thickness of the substrate 10 is equal to or smaller than 2 μm, for example. Therefore, the heat capacity of the substrate 10 is low, and the power consumption of the heater 12 can be reduced.

The heater 12 heats a solid electrolyte 20 in order to enable ion conduction in the solid electrolyte 20. The heater 12 is disposed over the substrate 10. Concretely, the heater 12 is formed over the upper surface of the substrate 10 with the intermediary of the insulating layer 11. The insulating layer 11 is formed of silicon dioxide ($SiO_2$) or aluminum oxide ($Al_2O_3$), for example. The heater 12 is disposed on the insulating layer 11. The insulating layer 11 electrically insulates the heater 12 and the substrate 10. The heater 12 is a platinum (Pt) thin-film heater or a poly-silicon thin-film heater, for example. The insulating layer 13 is disposed on the heater 12. The heater 12 is sandwiched by the insulating layer 11 and the insulating layer 13. The insulating layer 13 is formed of silicon dioxide ($SiO_2$) or aluminum oxide ($Al_2O_3$), for example.

The heater 12 may be formed on the lower surface of the substrate 10. For example, a layer-stacked body composed of the insulating layer 11, the heater 12, and the insulating layer 13 may be formed on the lower surface of the substrate 10. The heater 12 may be buried in the substrate 10. For example, a layer-stacked body composed of the insulating layer 11, the heater 12, and the insulating layer 13 may be buried in the substrate 10.

In the present embodiment, at least one limiting current-type gas sensor element 3 is formed over the upper surface of the substrate 10. The limiting current-type gas sensor element 3 mainly includes a gas introduction path 16, a first electrode 17, the solid electrolyte 20, and a second electrode 27. The limiting current-type gas sensor element 3 may further include a gas discharge path 30 and an insulating film 32. The limiting current-type gas sensor element 3 may further include insulating layers 15, 22, 23, 25, and 28.

The insulating layer 15 is disposed on the insulating layer 13. The insulating layer 15 is a tantalum pentoxide ($Ta_2O_5$) layer, for example.

The gas introduction path 16 is disposed over the insulating layer 13 with the intermediary of the insulating layer 15. The gas introduction path 16 extends between a gas inlet 35 and a first part 17d opposed to the solid electrolyte 20 in the first electrode 17. The length of the gas introduction path 16 in the direction along the upper surface of the substrate 10 (left-right direction in FIG. 2) is equal to or longer than ten times the thickness of the gas introduction path 16, for example. The length of the gas introduction path 16 in the direction along the upper surface of the substrate 10 (left-right direction in FIG. 2) is equal to or longer than ten times the thickness of the first electrode 17, for example.

The gas introduction path 16 is formed of a first porous transition metal oxide having a second melting point higher than a first melting point of the first electrode 17. The gas introduction path 16 is formed of the first porous transition metal oxide having a second melting point higher than a third melting point of the second electrode 27. In the present specification, the transition metals mean the elements of Group 3 to Group 11 in the long periodic table of elements by International Union of Pure and Applied Chemistry (IUPAC). The first porous transition metal oxide is tantalum pentoxide ($Ta_2O_5$), titanium dioxide ($TiO_2$), or chromium oxide (III) ($Cr_2O_3$), for example.

In order to enable conduction of ions in the solid electrolyte 20, the limiting current-type gas sensor 2 operates at a high temperature that is at least 400° C. and at most 750° C., for example, by using the heater 12. Further, the gas introduction path 16 is formed of the first porous transition metal oxide having the second melting point higher than the first melting point of the first electrode 17. For this reason, when the limiting current-type gas sensor 2 is operated at the high temperature, pores aggregate in the first electrode 17, whereas pores remain uniformly distributed in the gas introduction path 16. Thus, the gas introduction path 16 is more permeable to the measurement-target gas 4 than the first electrode 17.

A first filling rate of the gas introduction path 16 is equal to or lower than 60%, for example. The first filling rate of the gas introduction path 16 may be equal to or lower than 45%, for example. The gas introduction path 16 formed of the first porous transition metal oxide is obtained by obliquely evaporating a transition metal oxide, for example. The gas introduction path 16 formed of the first porous transition metal oxide may be obtained by sintering powders of a transition metal oxide, and the gas introduction path 16 may be a porous transition metal oxide sintered body. The gas introduction path 16 limits the amount of flow of the measurement-target gas 4 to the solid electrolyte 20 per unit time.

When the first filling rate of the gas introduction path 16 decreases and the porosity of the gas introduction path 16 increases, it becomes easier for the measurement-target gas 4 to pass through the gas introduction path 16 and the response time of the limiting current-type gas sensor 2 can be shortened. When the porosity of the gas introduction path 16 increases, thermal distortion caused in the solid electrolyte 20 at the time of operation of the limiting current-type gas sensor 2 can be alleviated by the gas introduction path 16. Variation in the temperature coefficient of the limiting current value of the limiting current-type gas sensor 2 can be reduced.

In the present specification, the filling rate of a certain layer is calculated as follows. The reflection spectrum of this layer is obtained. An optical thickness nd of this layer is calculated from this reflection spectrum. "n" represents the refractive index of this layer and "d" represents the physical thickness of this layer. Then, a scanning electron microscope (SEM) cross-sectional image of this layer is acquired. The physical thickness d of this layer is obtained from the SEM cross-sectional image of this layer. The refractive index n of this layer is obtained from the optical thickness nd of this layer and the physical thickness d of this layer. A refractive index $n_{100}$ when the filling rate of this layer is 100% is obtained, in advance. In general, it turns out that the filling rate of this layer is proportional to $(n^2-1)/(n^2+2)$ from the Lorentz-Lorenz equation. Thus, the ratio of $(n^2-1)/(n^2+2)$ to $(n_{100}^2-1)/(n_{100}^2+2)$ is calculated, so that the filling rate of this layer is calculated.

The first electrode 17 is disposed on the gas introduction path 16. The first electrode 17 is disposed on the solid electrolyte 20. Specifically, the first electrode 17 is disposed on a first surface 20a of the solid electrolyte 20 opposed to the substrate 10 (lower surface of the solid electrolyte 20). The first part 17d of the first electrode 17 is opposed to the first surface 20a of the solid electrolyte 20. The first electrode 17 is disposed between the solid electrolyte 20 and the gas introduction path 16. The first part 17d of the first electrode 17 is the part sandwiched between the solid electrolyte 20 and the gas introduction path 16 in the normal direction of the upper surface of the substrate 10 in the first electrode 17. The first part 17d of the first electrode 17 may be in contact with the first surface 20a of the solid electrolyte 20.

The first electrode 17 is a first porous metal electrode. Thus, the first electrode 17 allows the measurement-target gas 4 to readily pass through it toward the solid electrolyte 20. The first melting point of the first electrode 17 is lower than the second melting point of the first porous transition metal oxide that configures the gas introduction path 16. The first melting point of the first electrode 17 is lower than a fourth melting point of a second porous transition metal oxide that configures the gas discharge path 30. The first electrode 17 is formed of platinum (Pt) or palladium (Pd), for example.

The thickness of the first electrode 17 is at least 0.1 μm and at most 10 μm, for example. The first electrode 17 may extend to the gas inlet 35. The length of the first electrode 17 in the direction along the upper surface of the substrate 10 (left-right direction in FIG. 2) is equal to or longer than ten times the thickness of the first electrode 17, for example. For this reason, when pores of the first electrode 17 aggregate at the time of operation of the limiting current-type gas sensor 2 at a high temperature, the permeability of the first electrode 17 to the measurement-target gas 4 greatly decreases in the direction along the upper surface of the substrate 10 (left-right direction in FIG. 2), whereas the permeability of the first electrode 17 to the measurement-target gas 4 is comparatively high in the thickness direction of the first electrode 17 (upward-downward direction in FIG. 2). The gas introduction path 16 is more permeable to the measurement-target gas 4 than the first electrode 17 at the time of operation of the limiting current-type gas sensor 2 at the high temperature. Although the first electrode 17 extends to the gas inlet 35, the measurement-target gas 4 flows mainly in the gas introduction path 16.

The solid electrolyte 20 is disposed on the first electrode 17. The solid electrolyte 20 includes the first surface 20a (lower surface) opposed to the substrate 10 and a second surface 20b (upper surface) on the opposite side to the first surface 20a. The solid electrolyte 20 is an ion conductor such as an oxygen ion conductor. For example, the solid electrolyte 20 is an oxygen ion conductor in which CaO, MgO, $Y_2O_3$, $Yb_2O_3$, or the like is added as a stabilizer to a base material such as $ZrO_2$, $HfO_2$, $ThO_2$, or $Bi_2O_3$. Specifically, the solid electrolyte 20 is formed of yttria-stabilized zirconia (YSZ). The solid electrolyte 20 may be an oxygen ion conductor formed of $(La, Sr, Ga, Mg, Co)O_3$, for example. The solid electrolyte 20 has ion conductivity by being heated by the heater 12. At the time of operation of the limiting current-type gas sensor 2, the solid electrolyte 20 is heated at a temperature that is at least 400° C. and at most 750° C., for example, by using the heater 12.

The solid electrolyte 20 is a thin film having a thickness that is at least 1 μm and at most 10 μm, for example, and the limiting current-type gas sensor 2 is a thin-film limiting current-type gas sensor. The solid electrolyte 20 may be a bulk having a thickness equal to or larger than 100 μm, for example, and the limiting current-type gas sensor 2 may be a bulk limiting current-type gas sensor.

The insulating layer 22 is disposed on the insulating layer 13, the side surface of the gas introduction path 16, the side surface of the first electrode 17, the side surface of the solid electrolyte 20, and a part of the second surface 20b. The insulating layer 22 is a tantalum pentoxide ($Ta_2O_5$) layer, for example. The insulating layer 23 is disposed on the insulating layer 22. The insulating layer 23 is a silicon dioxide ($SiO_2$) layer, for example. The insulating layer 25 is disposed on the side surface of the insulating layer 22 and on the insulating layer 23. The insulating layer 25 is a titanium dioxide ($TiO_2$) layer, for example. A first opening and a second opening are made in the insulating layer 22, the insulating layer 23, and the insulating layer 25. A part of the second surface 20b of the solid electrolyte 20 is exposed from the first opening. The first electrode 17 is exposed from the second opening. The second opening functions as the gas inlet 35. When the first electrode 17 does not extend to the gas inlet 35, the gas introduction path 16 is exposed from the second opening.

The second electrode 27 is disposed on the solid electrolyte 20. Specifically, the second electrode 27 is disposed on the second surface 20b of the solid electrolyte 20 (upper surface of the solid electrolyte 20). A second part 27d of the second electrode 27 is opposed to the second surface 20b of the solid electrolyte 20. The second part 27d of the second electrode 27 is the part opposed to the second surface 20b of the solid electrolyte 20 in the normal direction of the upper surface of the substrate 10 in the second electrode 27. The second part 27d of the second electrode 27 may be in contact with the second surface 20b of the solid electrolyte 20. The second electrode 27 is disposed between the solid electrolyte 20 and the gas discharge path 30.

The second electrode 27 is a second porous metal electrode. Thus, the second electrode 27 allows the gas to readily pass through it toward the gas discharge path 30. The third melting point of the second electrode 27 is lower than the second melting point of the first porous transition metal oxide that configures the gas introduction path 16. The third melting point of the second electrode 27 is lower than the fourth melting point of the second porous transition metal oxide that configures the gas discharge path 30. The second electrode 27 is formed of platinum (Pt) or palladium (Pd), for example.

The second electrode 27 is disposed on the insulating layer 25. The second electrode 27 is disposed in the first opening made in the insulating layer 22, the insulating layer 23, and the insulating layer 25. The thickness of the second electrode 27 is at least 0.1 µm and at most 10 µm, for example. The second electrode 27 may extend to a gas outlet 36. The length of the second electrode 27 in the direction along the upper surface of the substrate 10 (left-right direction in FIG. 2) is equal to or longer than ten times the thickness of the second electrode 27, for example. For this reason, when pores of the second electrode 27 aggregate at the time of operation of the limiting current-type gas sensor 2 at a high temperature, the permeability of the second electrode 27 to the gas greatly decreases in the direction along the upper surface of the substrate 10 (left-right direction in FIG. 2), whereas the permeability of the second electrode 27 to the gas is comparatively high in the thickness direction of the second electrode 27 (upward-downward direction in FIG. 2).

The insulating layer 28 is disposed on the second electrode 27. The insulating layer 28 is a titanium dioxide ($TiO_2$) layer, for example.

The gas discharge path 30 is disposed on the insulating layer 28. The gas discharge path 30 extends between the gas outlet 36 and the second part 27d opposed to the solid electrolyte 20 in the second electrode 27. The length of the gas discharge path 30 in the direction along the upper surface of the substrate 10 (left-right direction in FIG. 2) is equal to or longer than ten times the thickness of the gas discharge path 30, for example. The length of the gas discharge path 30 in the direction along the upper surface of the substrate 10 (left-right direction in FIG. 2) is equal to or longer than ten times the thickness of the second electrode 27, for example.

The gas discharge path 30 is formed of the second porous transition metal oxide having the fourth melting point higher than the first melting point of the first electrode 17. The gas discharge path 30 is formed of the second porous transition metal oxide having the fourth melting point higher than the third melting point of the second electrode 27. The second porous transition metal oxide is tantalum pentoxide ($Ta_2O_5$), titanium dioxide ($TiO_2$), or chromium oxide (III) ($Cr_2O_3$).

When the limiting current-type gas sensor 2 is operated at a high temperature in order to enable conduction of ions in the solid electrolyte 20, pores aggregate in the second electrode 27, whereas pores remain uniformly distributed in the gas discharge path 30. Thus, the gas discharge path 30 is more permeable to the gas than the second electrode 27. Although the second electrode 27 extends to the gas outlet 36, the gas flows mainly in the gas discharge path 30.

A second filling rate of the gas discharge path 30 is equal to or lower than 60%, for example. The second filling rate of the gas discharge path 30 may be equal to or lower than 45%, for example. The gas discharge path 30 formed of the second porous transition metal oxide is obtained by obliquely evaporating a transition metal oxide, for example. The gas discharge path 30 formed of the second porous transition metal oxide may be obtained by sintering powders of a transition metal oxide, and the gas discharge path 30 may be a porous transition metal oxide sintered body.

When the second filling rate of the gas discharge path 30 decreases and the porosity of the gas discharge path 30 increases, it becomes easier for the gas to pass through the gas discharge path 30 and the response time of the limiting current-type gas sensor 2 can be shortened. When the porosity of the gas discharge path 30 increases, thermal distortion caused in the solid electrolyte 20 at the time of operation of the limiting current-type gas sensor 2 can be alleviated by the gas discharge path 30. Variation in the temperature coefficient of the limiting current value of the limiting current-type gas sensor 2 can be reduced.

The insulating film 32 covers a layer-stacked body composed of the first part 17d of the first electrode 17, the solid electrolyte 20, and the second part 27d of the second electrode 27. The insulating film 32 further covers the part opposed to the second part 27d of the second electrode 27 in the gas discharge path 30. The insulating film 32 is remoter from the substrate 10 than the second electrode 27. Moreover, the insulating film 32 is disposed on the insulating layer 25, on the side surface of the second electrode 27, and on the side surface of the insulating layer 28. The insulating film 32 is a silicon dioxide ($SiO_2$) layer, for example.

As illustrated in FIG. 1, the voltage source 5 is connected to the limiting current-type gas sensor 2 (the limiting current-type gas sensor element 3). Concretely, a negative electrode of the voltage source 5 is connected to the first electrode 17 of the limiting current-type gas sensor 2 (the limiting current-type gas sensor element 3). A positive electrode of the voltage source 5 is connected to the second electrode 27 of the limiting current-type gas sensor 2 (the limiting current-type gas sensor element 3). The voltage source 5 supplies a first voltage $V_1$ (see FIG. 3) and a second voltage $V_2$ (see FIG. 3) higher than the first voltage $V_1$ to the limiting current-type gas sensor 2 (the limiting current-type gas sensor element 3). The first voltage $V_1$ is a voltage that generates a first limiting current corresponding to the first gas in the limiting current-type gas sensor 2 (the limiting current-type gas sensor element 3). The second voltage $V_2$ is a voltage that generates a second limiting current corresponding to the second gas in the limiting current-type gas sensor 2 (the limiting current-type gas sensor element 3). The voltage source 5 can switch the voltage output to the limiting current-type gas sensor 2 between the first voltage $V_1$ and the second voltage $V_2$.

The current detector 6 is connected to the limiting current-type gas sensor 2 (the limiting current-type gas sensor element 3). Concretely, the current detector 6 is connected to the first electrode 17 and the second electrode 27 of the limiting current-type gas sensor 2 (the limiting current-type gas sensor element 3). Because the flow rate of the measurement-target gas 4 to the solid electrolyte 20 is limited by the gas introduction path 16, the current that passes through the solid electrolyte and flows between the first electrode 17 and the second electrode 27 is constant even when the voltage between the first electrode 17 and the second electrode 27 is increased. This constant current is referred to as the limiting current. The current detector 6 acquires a first limiting current value $I_1$ (see FIG. 3) of the limiting current-type gas sensor 2 when the first voltage $V_1$ is applied to the limiting current-type gas sensor 2 (the limiting current-type gas sensor element 3) and a second limiting current value $I_2$ (see FIG. 3) of the limiting current-type gas sensor 2 when the second voltage $V_2$ is applied to the limiting current-type gas sensor 2 (the limiting current-type gas sensor element 3). The limiting current value means the magnitude of the limiting current of the limiting current-type gas sensor 2 (the limiting current-type gas sensor element 3).

When the first voltage $V_1$ is being applied to the limiting current-type gas sensor 2, the first limiting current attributed to the first gas flows in the limiting current-type gas sensor 2. The first limiting current value $I_1$ is proportional to the concentration of the first gas (for example, oxygen ($O_2$)) contained in the measurement-target gas 4 (for example, exhaust gas). In contrast, because the second voltage $V_2$ is higher than the first voltage $V_1$, the first limiting current attributed to the first gas also flows in the limiting current-type gas sensor 2 in addition to the limiting current attributed to the second gas when the second voltage $V_2$ is being applied to the limiting current-type gas sensor 2. The second limiting current value $I_2$ is given as the sum of the first limiting current value $I_1$ proportional to the concentration of the first gas (for example, oxygen ($O_2$)) and the limiting current value proportional to the concentration of the second gas (for example, nitrogen oxides ($NO_X$)).

The gas concentration arithmetic unit 8 is connected to the current detector 6. The gas concentration arithmetic unit 8 includes a difference acquiring section 8a and a gas concentration acquiring section 8g.

The difference acquiring section 8a acquires a difference $\Delta I$ (see FIG. 3) between the second limiting current value $I_2$ and the first limiting current value $I_1$. Concretely, the difference $\Delta I$ is obtained by subtracting the first limiting current value $I_1$ from the second limiting current value $I_2$. As described above, the second limiting current value $I_2$ is given as the sum of the first limiting current value $I_1$ proportional to the concentration of the first gas (for example, oxygen ($O_2$)) and the limiting current value proportional to the concentration of the second gas (for example, nitrogen oxides ($NO_X$)). Thus, the limiting current value proportional to the concentration of the second gas (for example, nitrogen oxides ($NO_X$)) is obtained by subtracting the first limiting current value $I_1$ from the second limiting current value $I_2$.

In one example, the gas concentration arithmetic unit 8 includes an arithmetic processing device formed mainly of a semiconductor material. In the arithmetic processing device, a program to calculate the difference $\Delta I$ between the second limiting current value $I_2$ and the first limiting current value $I_1$ is executed. The difference acquiring section 8a is a part of the processing of the program executed by the arithmetic processing device. This processing is stored in the memory 9 such as a read-only memory (ROM) or a random access memory (RAM), for example.

In another example, as illustrated in FIG. 4, the difference acquiring section 8a may be configured by an electrical circuit. Concretely, the difference acquiring section 8a may include an amplifier circuit 40 and a difference circuit 50. The amplifier circuit 40 is connected to the limiting current-type gas sensor 2 (the limiting current-type gas sensor element 3). The amplifier circuit 40 amplifies the first signal corresponding to the first limiting current value $I_1$ and the second signal corresponding to the second limiting current value $I_2$. The amplifier circuit 40 includes an operational amplifier 41 and a resistor 42, for example.

The difference circuit 50 outputs a difference voltage between the first signal amplified by the amplifier circuit 40 and the second signal amplified by the amplifier circuit 40. For example, the difference circuit 50 includes an operational amplifier 51, resistors 52, 53, 54, and 55, and a basic voltage 56. The difference circuit 50 further includes a first reference voltage 61, a second reference voltage 62, and a switch 63. The basic voltage 56 is an intermediate voltage between the first reference voltage 61 and the second reference voltage 62, for example. When the first limiting current value $I_1$ is obtained, the switch 63 is connected to the first reference voltage 61. When the second limiting current value $I_2$ is obtained, the switch 63 is connected to the second reference voltage 62. The difference circuit 50 can cause a first offset voltage of the amplifier circuit 40 (for example, the operational amplifier 41) superimposed on the first signal amplified by the amplifier circuit 40 and a second offset voltage of the amplifier circuit 40 (for example, the operational amplifier 41) superimposed on the second signal amplified by the amplifier circuit 40 to cancel out each other.

The gas concentration acquiring section 8g obtains the concentration of the second gas on the basis of the difference $\Delta I$ between the second limiting current value $I_2$ and the first limiting current value $I_1$. Concretely, the gas concentration acquiring section 8g is connected to the difference acquiring section 8a and the memory 9. The difference $\Delta I$ between the second limiting current value $I_2$ and the first limiting current value $I_1$ is input from the difference acquiring section 8a to the gas concentration acquiring section 8g. The kind of second gas is also input to the gas concentration acquiring section 8g. For example, the kind of second gas is stored in the memory 9 and the gas concentration acquiring section 8g reads out the kind of second gas from the memory 9. In the memory 9, a data table 9t (see FIG. 5) in which the kind of second gas, the difference $\Delta I$ between the second limiting current value $I_2$ and the first limiting current value $I_1$, and the second gas concentration are associated with each other is stored. The gas concentration acquiring section 8g refers to the data table 9t and obtains the concentration of the second gas corresponding to the kind of second gas and the difference $\Delta I$.

Figure 6:
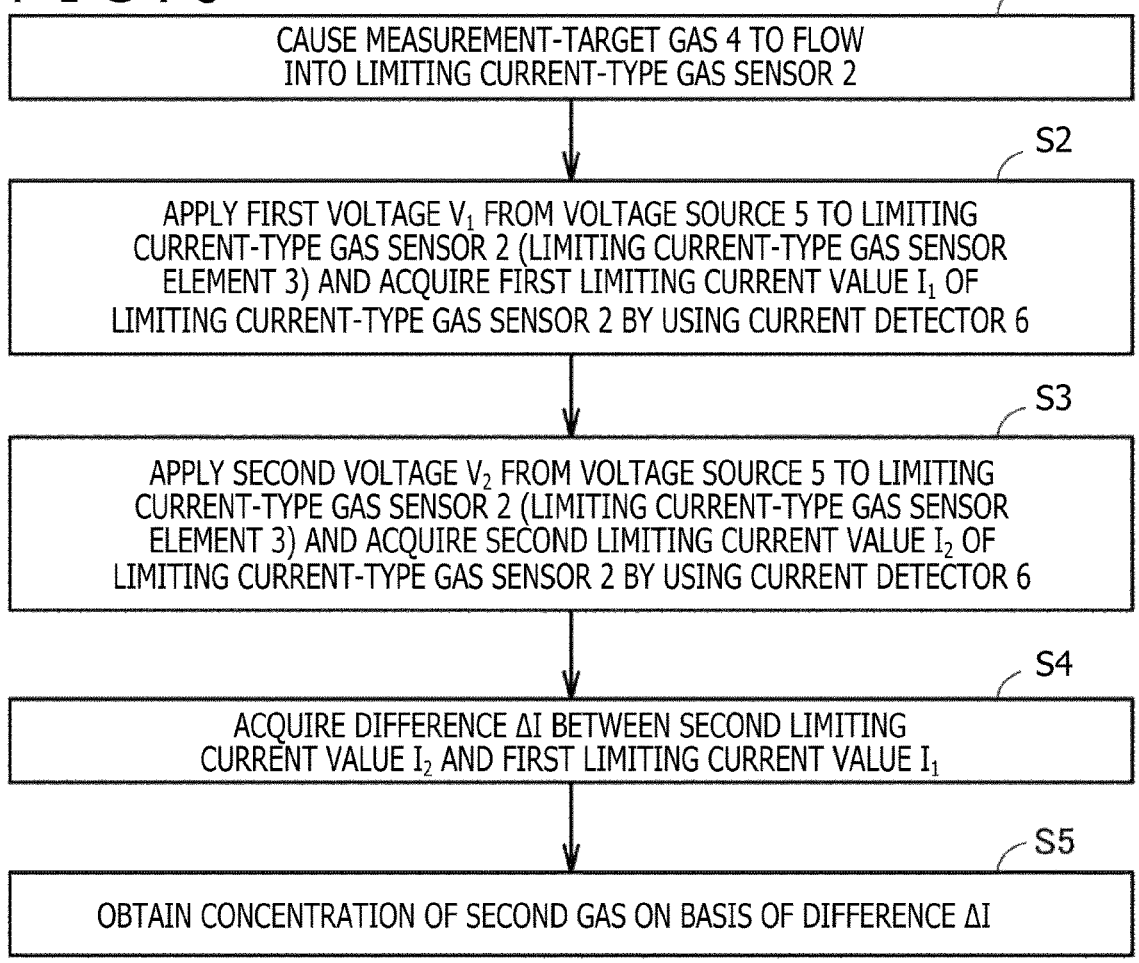
FIG. 6 is a diagram illustrating a flowchart of a gas concentration measurement method of embodiment 1.

A gas concentration measurement method of embodiment 1 will be described with reference to FIG. 6.

The gas concentration measurement method of the present embodiment causes the measurement-target gas 4 containing the first gas and the second gas to flow into the limiting current-type gas sensor 2 (the limiting current-type gas sensor element 3) (S1). The measurement-target gas 4 is the exhaust gas of an automobile, for example. The first gas is oxygen ($O_2$), for example. The second gas is nitrogen oxides ($NO_X$), for example. The measurement-target gas 4 passes mainly through the gas introduction path 16 and flows from the gas inlet 35 to the first electrode 17. The gas introduction path 16 limits the amount of flow of the measurement-target gas 4 to the solid electrolyte 20 per unit time.

The gas concentration measurement method of the present embodiment includes applying the first voltage $V_1$ from the voltage source 5 to the limiting current-type gas sensor 2 (the limiting current-type gas sensor element 3) and acquiring the first limiting current value $I_1$ of the limiting current-type gas sensor 2 by using the current detector 6 (S2). The first voltage $V_1$ is a voltage that generates the first limiting current corresponding to the first gas in the limiting current-type gas sensor 2 (the limiting current-type gas sensor element 3).

Concretely, the voltage source 5 applies the first voltage $V_1$ between the first electrode 17 and the second electrode 27. The first electrode 17 is connected to the negative electrode of the voltage source 5. The voltage source 5 supplies electrons to the first electrode 17. The first gas receives electrons at the interface between the first electrode 17 and the solid electrolyte 20 and is converted to first ions of a first element contained in the first gas. For example, the first gas is oxygen ($O_2$), and the first ions are oxygen ions ($2O^{2-}$). The solid electrolyte 20 is heated at a temperature that is at least 400° C. and at most 750° C., for example, by using the heater 12. The solid electrolyte 20 conducts the first ions from the first surface 20a of the solid electrolyte 20 to the second surface 20b of the solid electrolyte 20. Due to the conduction of the first ions, a current flows between the first electrode 17 and the second electrode 27.

Because the flow rate of the measurement-target gas 4 to the solid electrolyte 20 is limited by the gas introduction path 16, the current that flows between the first electrode 17 and the second electrode 27 is constant even when the voltage between the first electrode 17 and the second electrode 27 is increased. This constant current is the first limiting current. The first limiting current value $I_1$, which is the magnitude of the first limiting current, is proportional to the concentration of the first gas contained in the measurement-target gas 4. The first limiting current value $I_1$ is measured by the current detector 6.

The second electrode 27 is connected to the positive electrode of the voltage source 5. The voltage source 5 deprives the second electrode 27 of electrons. The first ions (for example, $2O^{2-}$) that have reached the second electrode 27 are deprived of electrons at the interface between the second electrode 27 and the solid electrolyte 20 and are converted to a gas (for example, $O_2$). The gas passes through the second electrode 27, which is the second porous metal electrode, and reaches the gas discharge path 30. The gas discharge path 30 is more permeable to the gas than the second electrode 27. The gas passes mainly through the gas discharge path 30 and is released from the gas outlet 36.

The gas concentration measurement method of the present embodiment includes applying the second voltage $V_2$ higher than the first voltage $V_1$ from the voltage source 5 to the limiting current-type gas sensor 2 (the limiting current-type gas sensor element 3) and acquiring the second limiting current value $I_2$ of the limiting current-type gas sensor 2 by using the current detector 6 (S3). The second voltage $V_2$ is a voltage that generates the second limiting current corresponding to the second gas in the limiting current-type gas sensor 2 (the limiting current-type gas sensor element 3).

Concretely, the voltage applied to the limiting current-type gas sensor 2 (the limiting current-type gas sensor element 3) is switched from the first voltage $V_1$ to the second voltage $V_2$. When the second gas is, for example, nitrogen oxides ($NO_X$), the first electrode 17 decomposes nitric oxide NO, which occupies a large part of the nitrogen oxides ($NO_X$), into nitrogen ($N_2$) and oxygen ($O_2$).

The first electrode 17 is connected to the negative electrode of the voltage source 5. The voltage source 5 supplies electrons to the first electrode 17. The oxygen ($O_2$) receives electrons at the interface between the first electrode 17 and the solid electrolyte 20 and is converted to second ions of a second element contained in the second gas. For example, the second ions are oxygen ions ($2O^{2-}$). The solid electrolyte 20 is heated at a temperature that is at least 400° C. and at most 750° C., for example, by using the heater 12. The solid electrolyte 20 conducts the second ions from the first surface 20a of the solid electrolyte 20 to the second surface 20b of the solid electrolyte 20. Due to the conduction of the second ions, a current flows between the first electrode 17 and the second electrode 27. The first ions of the first element contained in the first gas and the second ions of the second element contained in the second gas can both be conducted in the solid electrolyte 20. The second ions of the second element contained in the second gas may be the same as the first ions of the first element contained in the first gas.

Because the flow rate of the measurement-target gas 4 to the solid electrolyte 20 is limited by the gas introduction path 16, the current that flows between the first electrode 17 and the second electrode 27 is constant even when the voltage between the first electrode 17 and the second electrode 27 is increased. Because the second voltage $V_2$ is higher than the first voltage $V_1$, the first limiting current attributed to the first gas also flows in the limiting current-type gas sensor 2 in addition to the limiting current attributed to the second gas when the second voltage $V_2$ is being applied to the limiting current-type gas sensor 2 (the limiting current-type gas sensor element 3). The second limiting current value $I_2$ is given as the sum of the first limiting current value $I_1$ proportional to the concentration of the first gas (for example, oxygen ($O_2$)) and the limiting current value proportional to the concentration of the second gas (for example, nitrogen oxides ($NO_X$)). The second limiting current value $I_2$ is measured by the current detector 6.

The second electrode 27 is connected to the positive electrode of the voltage source 5. The voltage source 5 deprives the second electrode 27 of electrons. The second ions (for example, $2O^{2-}$) that have reached the second electrode 27 are deprived of electrons at the interface between the second electrode 27 and the solid electrolyte 20 and are converted to a gas (for example, $O_2$). The gas passes through the second electrode 27, which is the second porous metal electrode, and reaches the gas discharge path 30. The gas discharge path 30 is more permeable to the gas than the second electrode 27. The gas passes mainly through the gas discharge path 30 and is released from the gas outlet 36.

The gas concentration measurement method of the present embodiment includes acquiring the difference $\Delta I$ between the second limiting current value $I_2$ and the first limiting current value $I_1$ (S4). As described above, the second limiting current value $I_2$ is given as the sum of the first limiting current value $I_1$ proportional to the concentration of the first gas (for example, oxygen ($O_2$)) contained in the measurement-target gas 4 (for example, exhaust gas) and the limiting current value proportional to the concentration of the second gas (for example, nitrogen oxides ($NO_X$)) contained in the measurement-target gas 4 (for example, exhaust gas). Thus, the limiting current value proportional to the concentration of the second gas is obtained by subtracting the first limiting current value $I_1$ from the second limiting current value $I_2$. That is, the difference $\Delta I$ between the second limiting current value $I_2$ and the first limiting current value $I_1$ is proportional to the concentration of the second gas.

In one example, the gas concentration arithmetic unit 8 may include an arithmetic processing device formed mainly of a semiconductor material. In the arithmetic processing device, a program to calculate the difference $\Delta I$ between the second limiting current value $I_2$ and the first limiting current value $I_1$ may be executed. This processing is stored in the memory 9 such as a ROM or a RAM, for example.

In another example, as illustrated in FIG. 4, the difference $\Delta I$ between the second limiting current value $I_2$ and the first limiting current value $I_1$ may be acquired by the difference acquiring section 8a configured by an electrical circuit. Concretely, the difference acquiring section 8a may include the amplifier circuit 40 and the difference circuit 50. The amplifier circuit 40 amplifies the first signal corresponding to the first limiting current value $I_1$ and the second signal corresponding to the second limiting current value $I_2$. The amplifier circuit 40 includes the operational amplifier 41 and the resistor 42, for example.

The difference circuit 50 outputs a difference voltage between the first signal amplified by the amplifier circuit 40 and the second signal amplified by the amplifier circuit 40. For example, the difference circuit 50 includes the operational amplifier 51, the resistors 52, 53, 54, and 55, and the basic voltage 56. The difference circuit 50 further includes the first reference voltage 61, the second reference voltage 62, and the switch 63. The basic voltage 56 is an intermediate voltage between the first reference voltage 61 and the second reference voltage 62, for example. When the first limiting current value $I_1$ is obtained, the switch 63 is connected to the first reference voltage 61. When the second limiting current value $I_2$ is obtained, the switch 63 is connected to the second reference voltage 62. The difference circuit 50 can cause the first offset voltage of the amplifier circuit 40 (for example, the operational amplifier 41) superimposed on the first signal amplified by the amplifier circuit 40 and the second offset voltage of the amplifier circuit 40 (for example, the operational amplifier 41) superimposed on the second signal amplified by the amplifier circuit 40 to cancel out each other.

The gas concentration measurement method of the present embodiment further includes obtaining the concentration of the second gas on the basis of the difference $\Delta I$ between the second limiting current value $I_2$ and the first limiting current value $I_1$ (S5). Concretely, the difference $\Delta I$ between the second limiting current value $I_2$ and the first limiting current value $I_1$ obtained by the difference acquiring section 8a is input from the difference acquiring section 8a to the gas concentration acquiring section 8g. The kind of second gas is also input to the gas concentration acquiring section 8g. For example, the kind of second gas is stored in the memory 9, and the gas concentration acquiring section 8g reads out the kind of second gas from the memory 9. In the memory 9, the data table 9t (see FIG. 5) in which the kind of second gas, the difference $\Delta I$ between the second limiting current value $I_2$ and the first limiting current value $I_1$, and the second gas concentration are associated with each other is stored. The gas concentration acquiring section 8g refers to the data table 9t (see FIG. 5) and obtains the concentration of the second gas corresponding to the kind of second gas and the difference $\Delta I$.

Effects of the gas concentration measurement system 1 and the gas concentration measurement method of the present embodiment will be described.

The gas concentration measurement system 1 of the present embodiment includes the limiting current-type gas sensor 2, the voltage source 5 connected to the limiting current-type gas sensor 2, the current detector 6 connected to the limiting current-type gas sensor 2, and the gas concentration arithmetic unit 8 connected to the current detector 6. The voltage source 5 supplies the first voltage $V_1$ and the second voltage $V_2$ higher than the first voltage $V_1$ to the limiting current-type gas sensor 2. The first voltage $V_1$ is a voltage that generates the first limiting current corresponding to the first gas in the limiting current-type gas sensor 2. The second voltage $V_2$ is a voltage that generates the second limiting current corresponding to the second gas in the limiting current-type gas sensor 2. The current detector 6 acquires the first limiting current value $I_1$ of the limiting current-type gas sensor 2 when the first voltage $V_1$ is applied to the limiting current-type gas sensor 2 and the second limiting current value $I_2$ of the limiting current-type gas sensor 2 when the second voltage $V_2$ is applied to the limiting current-type gas sensor 2. The gas concentration arithmetic unit 8 includes the difference acquiring section 8a that acquires the difference $\Delta I$ between the second limiting current value $I_2$ and the first limiting current value $I_1$ and the gas concentration acquiring section 8g that obtains the concentration of the second gas on the basis of the difference $\Delta I$.

The second limiting current value $I_2$ is given as the sum of the first limiting current value $I_1$ proportional to the concentration of the first gas contained in the measurement-target gas 4 and the limiting current value proportional to the concentration of the second gas contained in the measurement-target gas 4. The limiting current value proportional to the concentration of the second gas is the difference $\Delta I$ between the second limiting current value $I_2$ and the first limiting current value $I_1$. Because the gas concentration measurement system 1 includes the difference acquiring section 8a that acquires the difference $\Delta I$ and the gas concentration acquiring section 8g that obtains the concentration of the second gas, the concentration of the second gas is obtained. Thus, in the gas concentration measurement system 1, a chamber for removing the first gas is unnecessary. The size of the gas concentration measurement system 1 can be reduced.

In the gas concentration measurement system 1 of the present embodiment, the voltage source 5 can switch the voltage output to the limiting current-type gas sensor 2 between the first voltage $V_1$ and the second voltage $V_2$. Thus, the concentration of the second gas is obtained as long as the limiting current-type gas sensor 2 includes at least one limiting current-type gas sensor element 3. The size of the gas concentration measurement system 1 can be reduced.

In the gas concentration measurement system 1 of the present embodiment, the difference acquiring section 8a includes the amplifier circuit 40 and the difference circuit 50. The amplifier circuit 40 amplifies the first signal corresponding to the first limiting current value $I_1$ and the second signal corresponding to the second limiting current value $I_2$. The difference circuit 50 outputs the difference $\Delta I$ between the first signal amplified by the amplifier circuit 40 and the second signal amplified by the amplifier circuit 40.

The difference circuit 50 can cause the first offset voltage of the amplifier circuit 40 (for example, the operational amplifier 41) superimposed on the first signal amplified by the amplifier circuit 40 and the second offset voltage of the amplifier circuit 40 (for example, the operational amplifier 41) superimposed on the second signal amplified by the amplifier circuit 40 to cancel out each other. More accurate concentration of the second gas is obtained.

In the gas concentration measurement system 1 of the present embodiment, the limiting current-type gas sensor 2 (the limiting current-type gas sensor element 3) includes the solid electrolyte 20, the first electrode 17, the second electrode 27, and the gas introduction path 16. The first electrode 17 is disposed on the solid electrolyte 20. The second electrode 27 is disposed on the solid electrolyte 20. The gas introduction path 16 extends between the gas inlet 35 and the first part 17d opposed to the solid electrolyte 20 in the first electrode 17. The first electrode 17 is the first porous metal electrode. The gas introduction path 16 is formed of the first porous transition metal oxide having the second melting point higher than the first melting point of the first electrode 17. The first porous transition metal oxide is $Ta_2O_5$, $TiO_2$, or $Cr_2O_3$.

Figure 7:
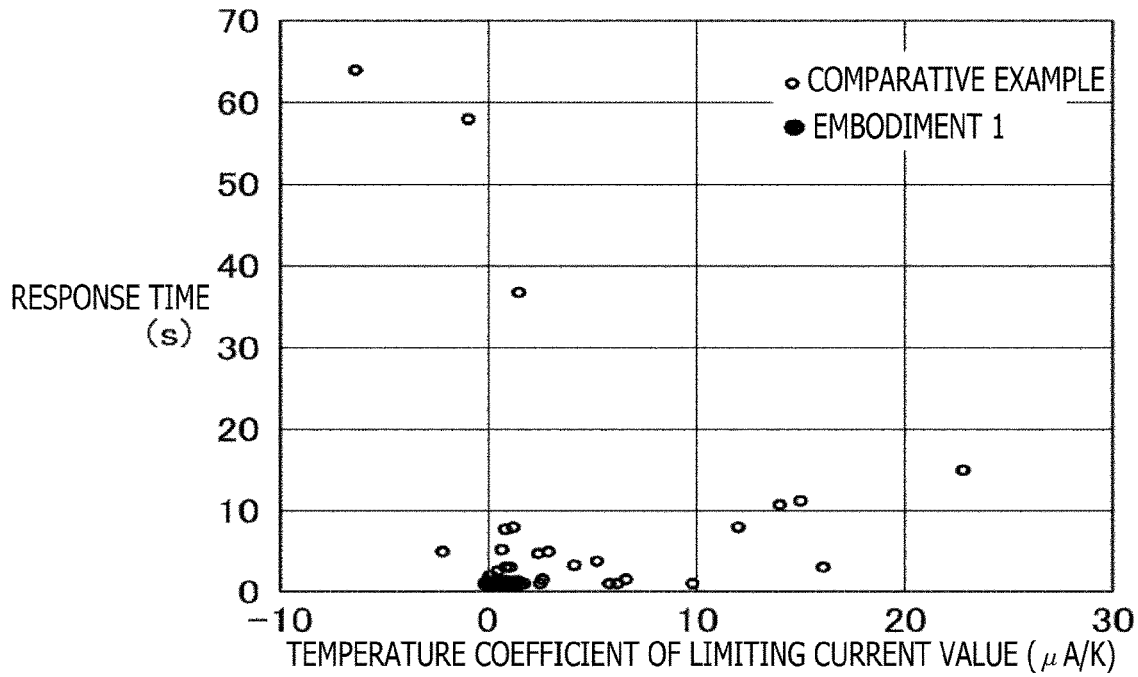
FIG. 7 is a diagram illustrating variation in a temperature coefficient of a limiting current value of a limiting current-type gas sensor of embodiment 1 and a limiting current-type gas sensor of a comparative example and variation in a response time of the limiting current-type gas sensor of embodiment 1 and the limiting current-type gas sensor of the comparative example.

Even when the limiting current-type gas sensor 2 (the limiting current-type gas sensor element 3) is operated at a high temperature, pores of the gas introduction path 16 formed of the first porous transition metal oxide hardly aggregate. Thus, as illustrated in FIG. 7, it is possible to reduce variation in the temperature coefficient of the limiting current value of the limiting current-type gas sensor 2 (plural limiting current-type gas sensor elements 3) and variation in the response time among plural limiting current-type gas sensors 2 (plural limiting current-type gas sensor elements 3). Even when the limiting current-type gas sensor 2 is operated at a high temperature, pores of the gas introduction path 16 formed of the first porous transition metal oxide hardly aggregate and the flow rate of the measurement-target gas 4 that passes through the gas introduction path 16 hardly changes. Thus, the response time of the limiting current-type gas sensor 2 can be shortened as illustrated in FIG. 7.

A limiting current-type gas sensor of a comparative example illustrated in FIG. 7 is different from the limiting current-type gas sensor 2 of the present embodiment in the following point. The limiting current-type gas sensor of the comparative example does not include the gas introduction path 16 formed of the first porous transition metal oxide and the gas discharge path 30 formed of the second porous transition metal oxide. In the limiting current-type gas sensor of the comparative example, the first electrode 17 that is a porous platinum electrode functions as the gas introduction path 16 and the second electrode 27 that is a porous platinum electrode functions as the gas discharge path.

Figure 8:
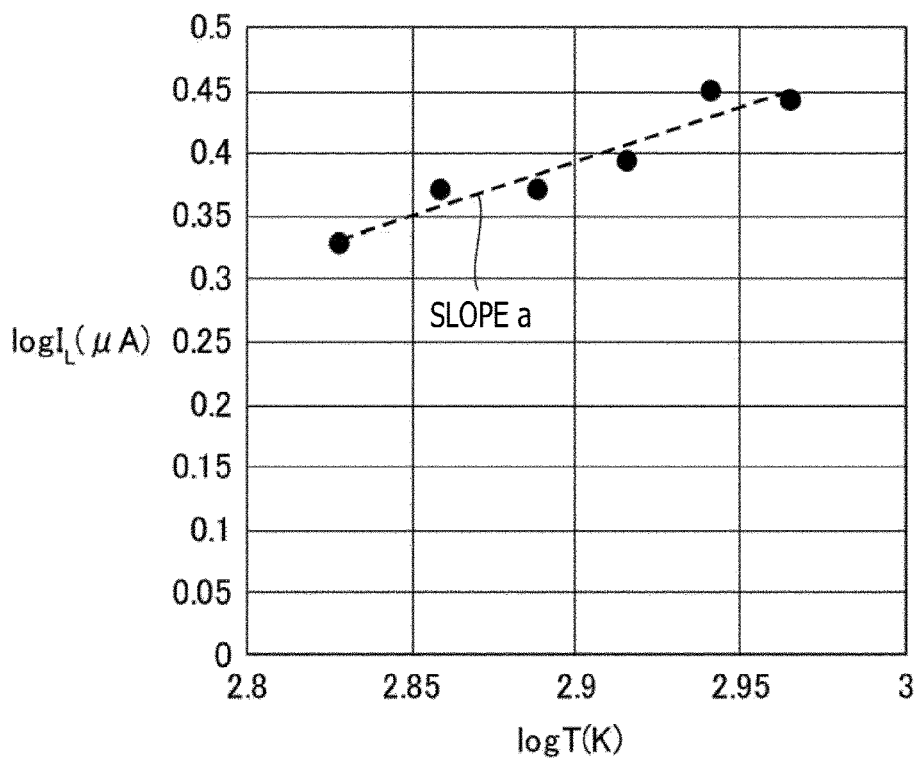
FIG. 8 is a diagram illustrating a calculation method of the temperature coefficient of the limiting current value of the limiting current-type gas sensor.

The temperature coefficient of the limiting current value of the limiting current-type gas sensor was calculated by the following method like one illustrated in FIG. 8. Plural samples were manufactured regarding the limiting current-type gas sensor of the comparative example. Plural samples were manufactured regarding the limiting current-type gas sensor 2 of the present embodiment. A limiting current value $I_L$ of each sample is measured while a temperature T of the sample is changed. Then, linear approximation is carried out regarding the relation between log T that is the logarithm of the temperature T and log $I_L$ that is the logarithm of the limiting current value $I_L$ by using the least squares method. A slope a of this approximate line is obtained as the temperature coefficient of the limiting current value of the limiting current-type gas sensor.

Figure 9:
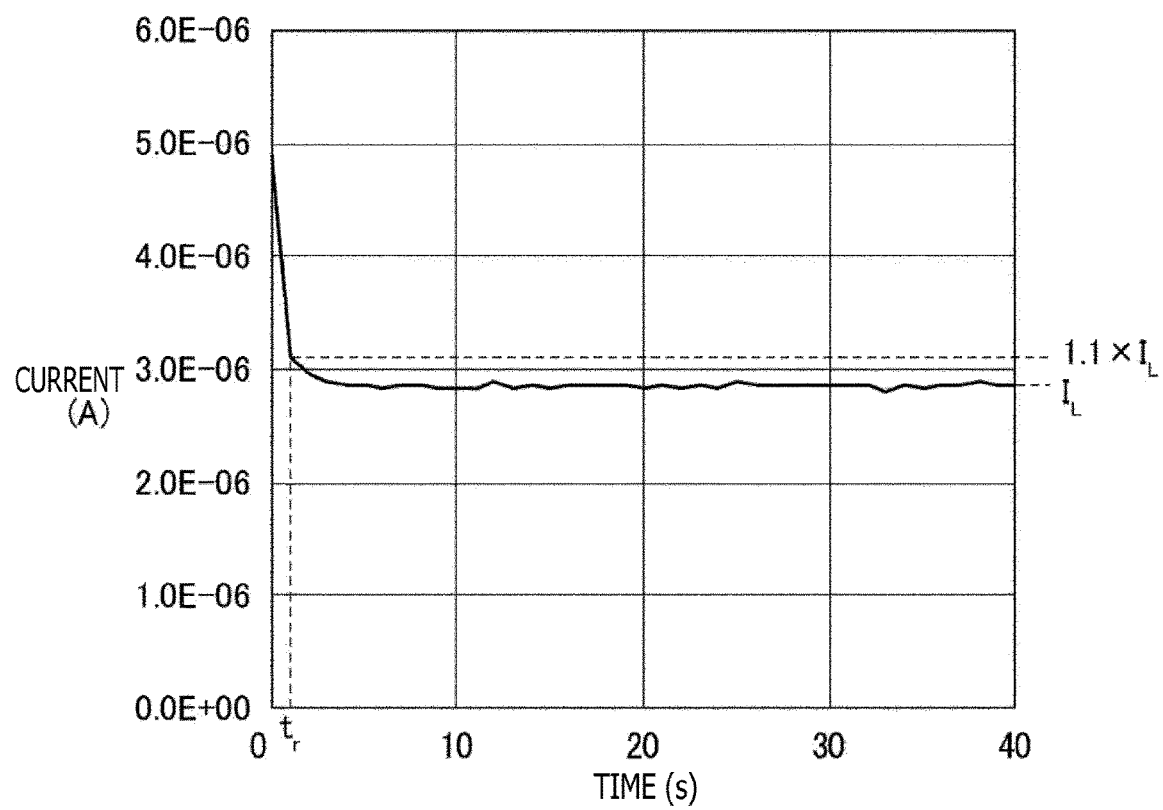
FIG. 9 is a diagram illustrating a calculation method of the response time of the limiting current value of the limiting current-type gas sensor.

A response time $t_r$ of the limiting current-type gas sensor was calculated by the following method like one illustrated in FIG. 9. Plural samples were manufactured regarding the limiting current-type gas sensor of the comparative example. Plural samples were manufactured regarding the limiting current-type gas sensor 2 of the present embodiment. Each sample is exposed to the measurement-target gas 4. At a time t=0, the voltage source 5 is connected to each sample. Time change of a current value output from each sample (transient response of the limiting current-type gas sensor) is measured. The average current value of a period during which the current value output from each sample can be regarded as constant is the limiting current value $I_L$ of the sample. Then, the time from the time t=0 until the current value output from each sample becomes 1.1 times the limiting current value $I_L$ is obtained as the response time $t_r$ of the sample.

The gas concentration measurement method of the present embodiment includes applying the first voltage $V_1$ from the voltage source 5 to the limiting current-type gas sensor 2 and acquiring the first limiting current value $I_1$ of the limiting current-type gas sensor 2 by using the current detector 6 (S2). The first voltage $V_1$ is a voltage that generates the first limiting current corresponding to the first gas in the limiting current-type gas sensor 2. The gas concentration measurement method of the present embodiment includes applying the second voltage $V_2$ higher than the first voltage $V_1$ from the voltage source 5 to the limiting current-type gas sensor 2 and acquiring the second limiting current value $I_2$ of the limiting current-type gas sensor 2 by using the current detector 6 (S3). The second voltage $V_2$ is a voltage that generates the second limiting current corresponding to the second gas in the limiting current-type gas sensor 2. The gas concentration measurement method of the present embodiment further includes acquiring the difference $\Delta I$ between the second limiting current value $I_2$ and the first limiting current value $I_1$ (S4) and obtaining the concentration of the second gas on the basis of the difference $\Delta I$ (S5).

The second limiting current value $I_2$ is given as the sum of the first limiting current value $I_1$ proportional to the concentration of the first gas contained in the measurement-target gas 4 and the limiting current value proportional to the concentration of the second gas contained in the measurement-target gas 4. The limiting current value proportional to the concentration of the second gas is the difference $\Delta I$ between the second limiting current value $I_2$ and the first limiting current value $I_1$. Because the gas concentration measurement method of the present embodiment includes acquiring the difference $\Delta I$ between the second limiting current value $I_2$ and the first limiting current value $I_1$ (S4) and obtaining the concentration of the second gas on the basis of the difference $\Delta I$ (S5), the concentration of the second gas is obtained. Thus, in the gas concentration measurement method of the present embodiment, a chamber for removing the first gas is unnecessary. The gas concentration measurement method of the present embodiment enables size reduction of the gas concentration measurement system 1.

The gas concentration measurement method of the present embodiment switches the voltage applied to the limiting current-type gas sensor 2 from the first voltage $V_1$ to the second voltage $V_2$ after the first limiting current value $I_1$ is acquired and before the second limiting current value $I_2$ is acquired. Thus, the concentration of the second gas is obtained as long as the limiting current-type gas sensor 2 includes at least one limiting current-type gas sensor element 3. The gas concentration measurement method of the present embodiment enables size reduction of the gas concentration measurement system 1.

Embodiment 2

Figure 10:
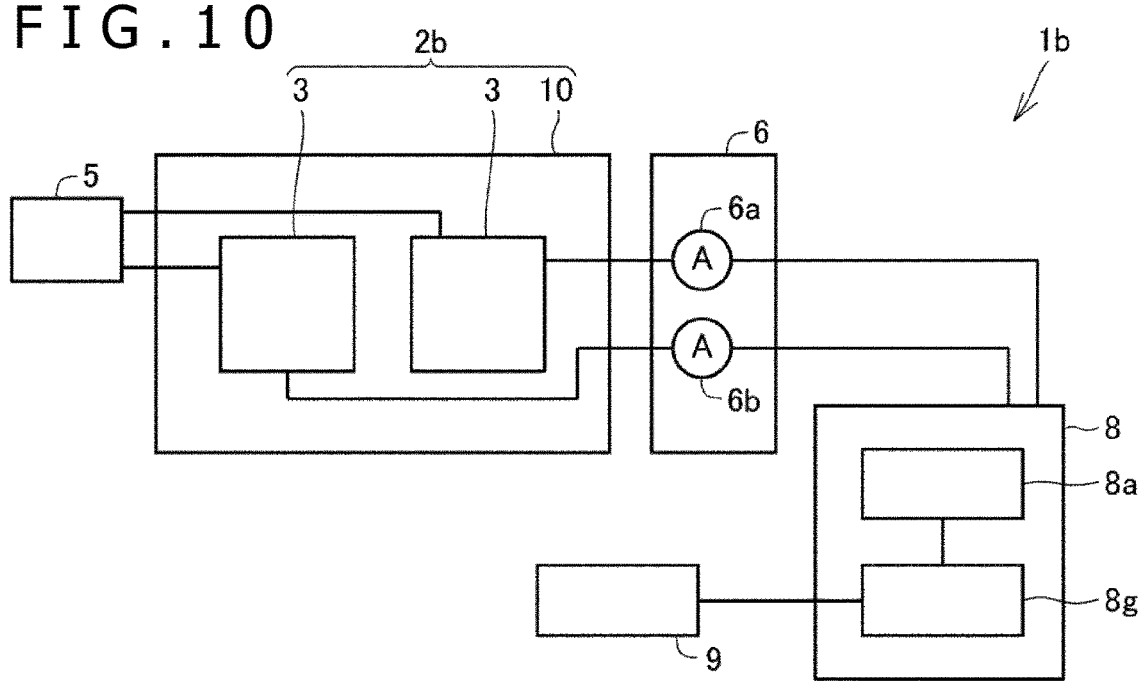
FIG. 10 is a schematic diagram of a gas concentration measurement system of embodiment 2.

A gas concentration measurement system 1b according to embodiment 2 will be described with reference to FIG. 10. The gas concentration measurement system 1b of the present embodiment has a configuration similar to that of the gas concentration measurement system 1 of embodiment 1 but is different mainly in the following points.

In the present embodiment, a limiting current-type gas sensor 2b includes plural limiting current-type gas sensor elements 3. The plural limiting current-type gas sensor elements 3 have the same configuration as each other. Concretely, the plural limiting current-type gas sensor elements 3 each include the solid electrolyte 20, the first electrode 17, the second electrode 27, and the gas introduction path 16. The first electrode 17 is disposed on the solid electrolyte 20. The second electrode 27 is disposed on the solid electrolyte 20. The gas introduction path 16 extends between the gas inlet 35 and the first part 17d opposed to the solid electrolyte 20 in the first electrode 17. The first electrode 17 is the first porous metal electrode. The gas introduction path 16 is formed of the first porous transition metal oxide having the second melting point higher than the first melting point of the first electrode 17. The first porous transition metal oxide is $Ta_2O_5$, $TiO_2$, or $Cr_2O_3$.

The current detector 6 includes plural current detecting elements 6a and 6b corresponding to respective ones of the plural limiting current-type gas sensor elements 3. The plural current detecting elements 6a and 6b acquire first plural limiting current values of the plural limiting current-type gas sensor elements 3 when the first voltage $V_1$ is applied to the plural limiting current-type gas sensor elements 3. The plural current detecting elements 6a and 6b acquire second plural limiting current values of the plural limiting current-type gas sensor elements 3 when the second voltage $V_2$ is applied to the plural limiting current-type gas sensor elements 3.

The difference acquiring section 8a calculates the average value of the difference between the second plural limiting current values and the first plural limiting current values as the difference ΔI between the second limiting current value $I_2$ and the first limiting current value $I_1$.

In one example, the average value of the difference between the second plural limiting current values and the first plural limiting current values is calculated by dividing the difference between the sum of the second plural limiting current values and the sum of the first plural limiting current values by the number of plural limiting current-type gas sensor elements 3. The difference between the sum of the second plural limiting current values and the sum of the first plural limiting current values is obtained by subtracting the sum of the first plural limiting current values from the sum of the second plural limiting current values.

In another example, the average value of the difference between the second plural limiting current values and the first plural limiting current values is calculated by calculating the difference between the limiting current value when the second voltage $V_2$ is applied and the limiting current value when the first voltage $V_1$ is applied regarding each of the plural limiting current-type gas sensor elements 3 and then calculating the average value of the plural differences of the plural limiting current-type gas sensor elements 3. Regarding each of the plural limiting current-type gas sensor elements 3, the difference between the limiting current value when the second voltage $V_2$ is applied and the limiting current value when the first voltage $V_1$ is applied is obtained by subtracting the limiting current value when the first voltage $V_1$ is applied from the limiting current value when the second voltage $V_2$ is applied. The average value of the plural differences is calculated by dividing the sum of the plural differences of the plural limiting current-type gas sensor elements 3 by the number of plural limiting current-type gas sensor elements 3.

Figure 11:
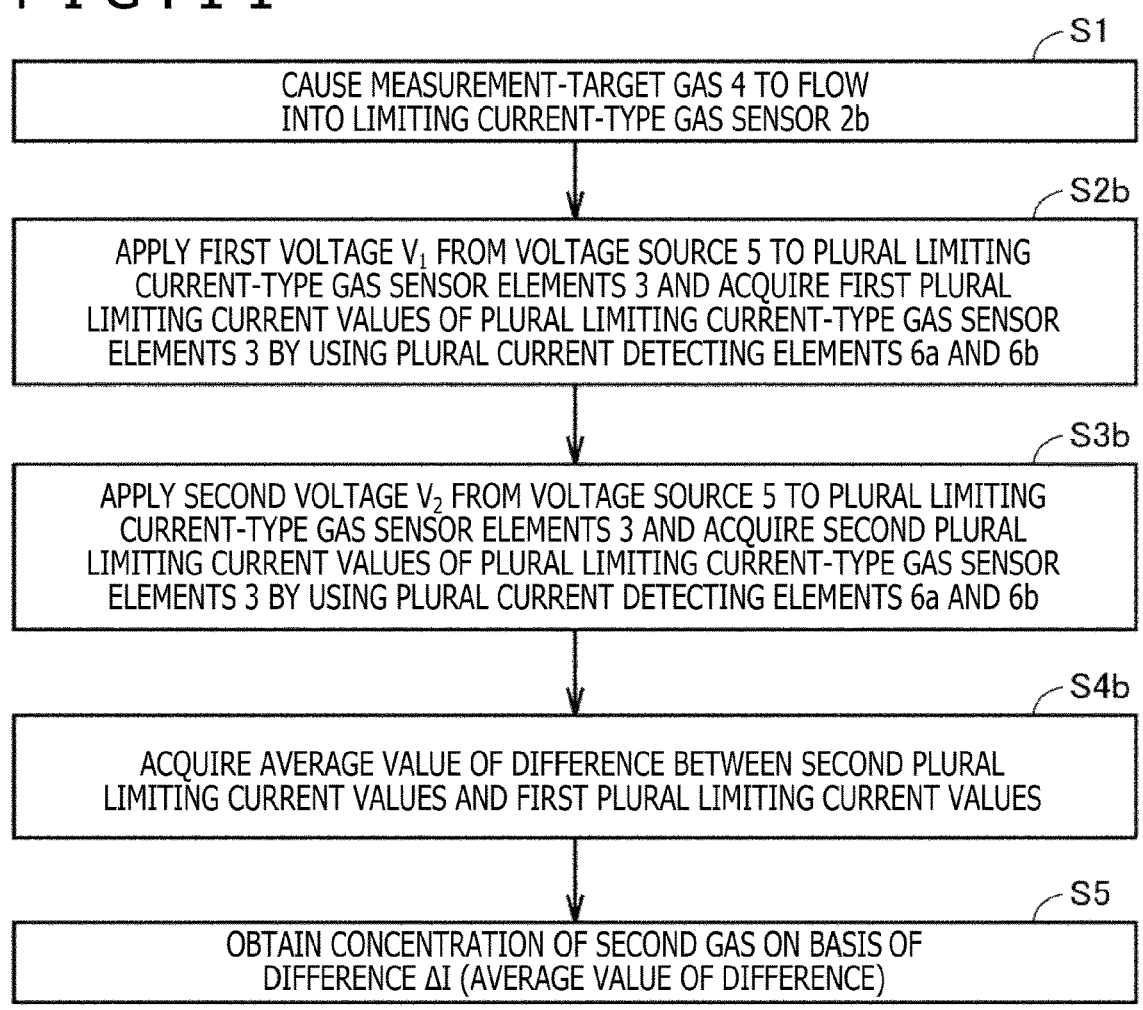
FIG. 11 is a diagram illustrating a flowchart of a gas concentration measurement method of embodiment 2.

A gas concentration measurement method according to embodiment 2 will be described with reference to FIG. 11. The gas concentration measurement method of the present embodiment includes steps similar to those of the gas concentration measurement method of embodiment 1 but is different mainly in the following points.

The gas concentration measurement method of the present embodiment includes applying the first voltage $V_1$ from the voltage source 5 to the plural limiting current-type gas sensor elements 3 and acquiring the first plural limiting current values of the plural limiting current-type gas sensor elements 3 by using the plural current detecting elements 6a and 6b (S2b) as acquiring the first limiting current value $I_1$ in embodiment 1 (S2). The gas concentration measurement method of the present embodiment includes applying the second voltage $V_2$ from the voltage source 5 to the plural limiting current-type gas sensor elements 3 and acquiring the second plural limiting current values of the plural limiting current-type gas sensor elements 3 by using the plural current detecting elements 6a and 6b (S3b) as acquiring the second limiting current value $I_2$ in embodiment 1 (S3).

The gas concentration measurement method of the present embodiment includes acquiring the average value of the difference between the second plural limiting current values and the first plural limiting current values (S4b) as acquiring the difference ΔI between the second limiting current value $I_2$ and the first limiting current value $I_1$ in embodiment 1 (S4). The difference acquiring section 8a calculates the average value of the difference between the second plural limiting current values and the first plural limiting current values. The average value of the difference between the second plural limiting current values and the first plural limiting current values is equivalent to the difference ΔI between the second limiting current value $I_2$ and the first limiting current value $I_1$.

In one example, the average value of the difference between the second plural limiting current values and the first plural limiting current values is calculated by dividing the difference between the sum of the second plural limiting current values and the sum of the first plural limiting current values by the number of plural limiting current-type gas sensor elements 3. The difference between the sum of the second plural limiting current values and the sum of the first plural limiting current values is obtained by subtracting the sum of the first plural limiting current values from the sum of the second plural limiting current values.

In another example, the average value of the difference between the second plural limiting current values and the first plural limiting current values is calculated by calculating the difference between the limiting current value when the second voltage $V_2$ is applied and the limiting current value when the first voltage $V_1$ is applied regarding each of the plural limiting current-type gas sensor elements 3 and then calculating the average value of the plural differences of the plural limiting current-type gas sensor elements 3. Regarding each of the plural limiting current-type gas sensor elements 3, the difference between the limiting current value when the second voltage $V_2$ is applied and the limiting current value when the first voltage $V_1$ is applied is obtained by subtracting the limiting current value when the first voltage $V_1$ is applied from the limiting current value when the second voltage $V_2$ is applied. The average value of the plural differences is calculated by dividing the sum of the plural differences of the plural limiting current-type gas sensor elements 3 by the number of plural limiting current-type gas sensor elements 3.

The gas concentration measurement system 1b and the gas concentration measurement method of the present embodiment provide the following effects in addition to the effects of the gas concentration measurement system 1 and the gas concentration measurement method of embodiment 1.

In the gas concentration measurement system 1b of the present embodiment, the limiting current-type gas sensor 2b includes the plural limiting current-type gas sensor elements 3. The current detector 6 includes the plural current detecting elements 6a and 6b corresponding to respective ones of the plural limiting current-type gas sensor elements 3. The plural current detecting elements 6a and 6b acquire the first plural limiting current values of the plural limiting current-type gas sensor elements 3 when the first voltage $V_1$ is applied to the plural limiting current-type gas sensor elements 3. The plural current detecting elements 6a and 6b acquire the second plural limiting current values of the plural limiting current-type gas sensor elements 3 when the second voltage $V_2$ is applied to the plural limiting current-type gas sensor elements 3. The difference ΔI between the second limiting current value $I_2$ and the first limiting current value $I_1$ is the average value of the difference between the second plural limiting current values and the first plural limiting current values.

In the gas concentration measurement method of the present embodiment, the limiting current-type gas sensor $2b$ includes the plural limiting current-type gas sensor elements 3. The current detector 6 includes the plural current detecting elements 6a and 6b corresponding to respective ones of the plural limiting current-type gas sensor elements 3. Acquiring the first limiting current value $I_1$ (S2) is applying the first voltage $V_1$ to the plural limiting current-type gas sensor elements 3 and acquiring the first plural limiting current values of the plural limiting current-type gas sensor elements 3 by using the plural current detecting elements 6a and 6b (S2b). Acquiring the second limiting current value $I_2$ (S3) is applying the second voltage $V_2$ to the plural limiting current-type gas sensor elements 3 and acquiring the second plural limiting current values of the plural limiting current-type gas sensor elements 3 by using the plural current detecting elements 6a and 6b (S3b). Acquiring the difference $\Delta I$ between the second limiting current value $I_2$ and the first limiting current value $I_1$ (S4) is acquiring the average value of the difference between the second plural limiting current values and the first plural limiting current values (S4b).

In the gas concentration measurement system $1b$ of the present embodiment and the gas concentration measurement method of the present embodiment, the concentration of the second gas is obtained on the basis of the average value of the difference between the second plural limiting current values and the first plural limiting current values. Even when variation exists in the current-voltage characteristic of the plural limiting current-type gas sensor elements 3, the concentration of the second gas can be obtained with improved accuracy.

Embodiment 3

Figure 12:
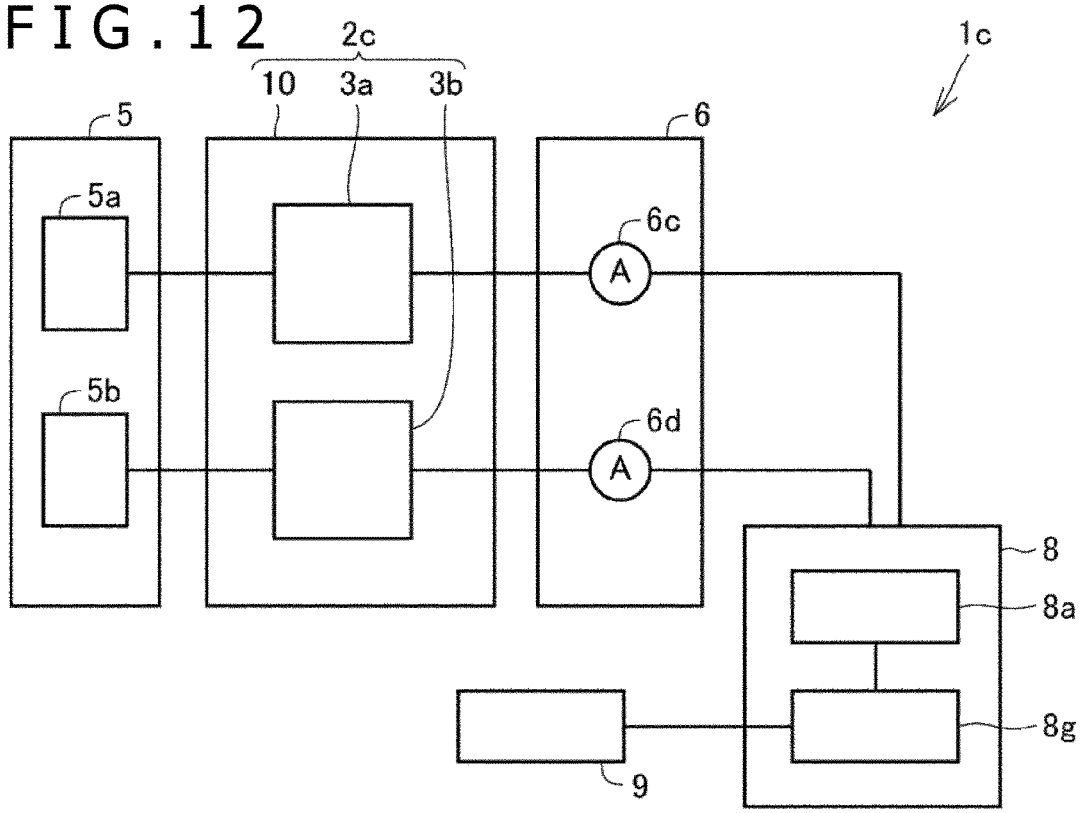
FIG. 12 is a schematic diagram of a gas concentration measurement system of embodiment 3.

A gas concentration measurement system $1c$ according to embodiment 3 will be described with reference to FIG. 12. The gas concentration measurement system $1c$ of the present embodiment has a configuration similar to that of the gas concentration measurement system 1 of embodiment 1 but is different mainly in the following points.

In the present embodiment, a limiting current-type gas sensor $2c$ includes a first limiting current-type gas sensor element $3a$ and a second limiting current-type gas sensor element $3b$. The first limiting current-type gas sensor element $3a$ and the second limiting current-type gas sensor element $3b$ have the same configuration as each other. For example, the first limiting current-type gas sensor element $3a$ and the second limiting current-type gas sensor element $3b$ each have the same configuration as the limiting current-type gas sensor element 3 of embodiment 1. Concretely, the first limiting current-type gas sensor element $3a$ and the second limiting current-type gas sensor element $3b$ each include the solid electrolyte 20, the first electrode 17, the second electrode 27, and the gas introduction path 16. The first electrode 17 is disposed on the solid electrolyte 20. The second electrode 27 is disposed on the solid electrolyte 20. The gas introduction path 16 extends between the gas inlet 35 and the first part $17d$ opposed to the solid electrolyte 20 in the first electrode 17. The first electrode 17 is the first porous metal electrode. The gas introduction path 16 is formed of the first porous transition metal oxide having the second melting point higher than the first melting point of the first electrode 17. The first porous transition metal oxide is $Ta_2O_5$, $TiO_2$, or $Cr_2O_3$.

The current detector 6 includes a first current detecting element $6c$ corresponding to the first limiting current-type gas sensor element $3a$ and a second current detecting element $6d$ corresponding to the second limiting current-type gas sensor element $3b$. The first current detecting element $6c$ acquires the limiting current value of the first limiting current-type gas sensor element $3a$ when the first voltage $V_1$ is applied to the first limiting current-type gas sensor element $3a$ as the first limiting current value $I_1$. The second current detecting element $6d$ acquires the limiting current value of the second limiting current-type gas sensor element $3b$ when the second voltage $V_2$ is applied to the second limiting current-type gas sensor element $3b$ as the second limiting current value $I_2$.

Specifically, the voltage source 5 may include a first voltage supplier $5a$ that supplies the first voltage $V_1$ to the first limiting current-type gas sensor element $3a$ and a second voltage supplier $5b$ that supplies the second voltage $V_2$ to the second limiting current-type gas sensor element $3b$. The second limiting current value $I_2$ (limiting current value of the second limiting current-type gas sensor element $3b$) may be acquired while the first limiting current value $I_1$ (limiting current value of the first limiting current-type gas sensor element $3a$) is acquired.

Figure 13:
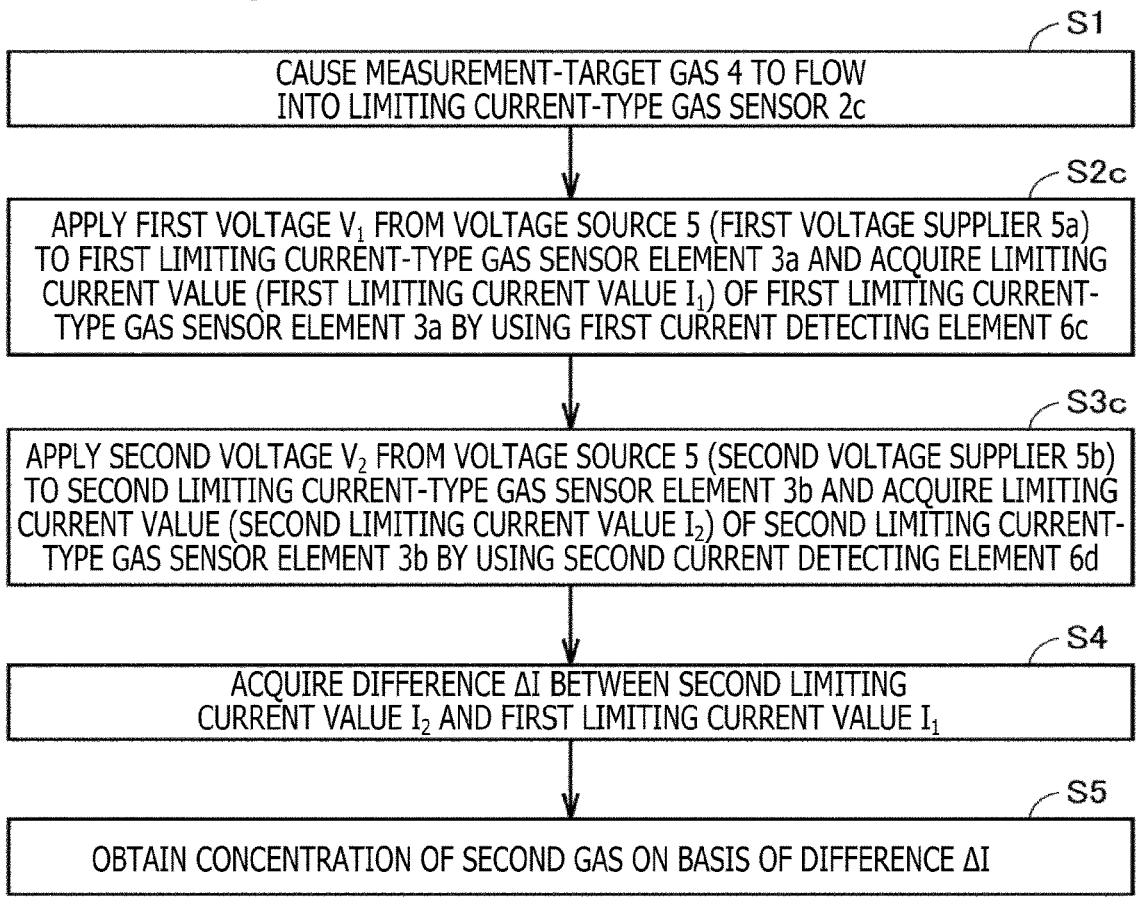
FIG. 13 is a diagram illustrating a flowchart of a gas concentration measurement method of embodiment 3.

A gas concentration measurement method according to embodiment 3 will be described with reference to FIG. 13. The gas concentration measurement method of the present embodiment includes steps similar to those of the gas concentration measurement method of embodiment 1 but is different mainly in the following points.

The gas concentration measurement method of the present embodiment includes applying the first voltage $V_1$ from the voltage source 5 (the first voltage supplier $5a$) to the first limiting current-type gas sensor element $3a$ and acquiring the limiting current value of the first limiting current-type gas sensor element $3a$ by using the first current detecting element $6c$ (S2c) as acquiring the first limiting current value $I_1$ in embodiment 1 (S2). The limiting current value of the first limiting current-type gas sensor element $3a$ is the first limiting current value $I_1$. The gas concentration measurement method of the present embodiment includes applying the second voltage $V_2$ from the voltage source 5 (the second voltage supplier $5b$) to the second limiting current-type gas sensor element $3b$ and acquiring the limiting current value of the second limiting current-type gas sensor element $3b$ by using the second current detecting element $6d$ (S3c) as acquiring the second limiting current value $I_2$ in embodiment 1 (S3). The limiting current value of the second limiting current-type gas sensor element $3b$ is the second limiting current value $I_2$.

Specifically, the voltage source 5 may include the first voltage supplier $5a$ that supplies the first voltage $V_1$ to the first limiting current-type gas sensor element $3a$ and the second voltage supplier $5b$ that supplies the second voltage $V_2$ to the second limiting current-type gas sensor element $3b$. The second limiting current value $I_2$ (limiting current value of the second limiting current-type gas sensor element $3b$) may be acquired while the first limiting current value $I_1$ (limiting current value of the first limiting current-type gas sensor element $3a$) is acquired.

The gas concentration measurement system $1c$ and the gas concentration measurement method of the present embodiment provide the following effects in addition to the effects of the gas concentration measurement system 1 and the gas concentration measurement method of embodiment 1.

In the gas concentration measurement system $1c$ of the present embodiment, the limiting current-type gas sensor $2c$ includes the first limiting current-type gas sensor element 3a and the second limiting current-type gas sensor element 3b. The current detector 6 includes the first current detecting element 6c corresponding to the first limiting current-type gas sensor element 3a and the second current detecting element 6d corresponding to the second limiting current-type gas sensor element 3b. The first current detecting element 6c acquires the limiting current value of the first limiting current-type gas sensor element 3a when the first voltage $V_1$ is applied to the first limiting current-type gas sensor element 3a as the first limiting current value $I_1$. The second current detecting element 6d acquires the limiting current value of the second limiting current-type gas sensor element 3b when the second voltage $V_2$ is applied to the second limiting current-type gas sensor element 3b as the second limiting current value $I_2$. Thus, a chamber for removing the first gas is unnecessary. The size of the gas concentration measurement system 1c can be reduced.

In the gas concentration measurement system 1c of the present embodiment, the voltage source 5 includes the first voltage supplier 5a that supplies the first voltage $V_1$ to the first limiting current-type gas sensor element 3a and the second voltage supplier 5b that supplies the second voltage $V_2$ to the second limiting current-type gas sensor element 3b. The first voltage supplier 5a and the second voltage supplier 5b make it possible to supply the second voltage $V_2$ to the second limiting current-type gas sensor element 3b while supplying the first voltage $V_1$ to the first limiting current-type gas sensor element 3a. The second limiting current value $I_2$ (limiting current value of the second limiting current-type gas sensor element 3b) can be acquired while the first limiting current value $I_1$ (limiting current value of the first limiting current-type gas sensor element 3a) is acquired. Thus, the time to measure the concentration of the second gas can be shortened.

In the gas concentration measurement method of the present embodiment, the limiting current-type gas sensor 2c includes the first limiting current-type gas sensor element 3a and the second limiting current-type gas sensor element 3b. The current detector 6 includes the first current detecting element 6c corresponding to the first limiting current-type gas sensor element 3a and the second current detecting element 6d corresponding to the second limiting current-type gas sensor element 3b. Acquiring the first limiting current value $I_1$ (S2) is applying the first voltage $V_1$ from the voltage source 5 (the first voltage supplier 5a) to the first limiting current-type gas sensor element 3a and acquiring the limiting current value of the first limiting current-type gas sensor element 3a by using the first current detecting element 6c (S2c). Acquiring the second limiting current value $I_2$ (S3) is applying the second voltage $V_2$ from the voltage source 5 (the second voltage supplier 5b) to the second limiting current-type gas sensor element 3b and acquiring the limiting current value of the second limiting current-type gas sensor element 3b by using the second current detecting element 6d (S3c). Thus, a chamber for removing the first gas is unnecessary. The gas concentration measurement method of the present embodiment enables size reduction of the gas concentration measurement system 1c.

In the gas concentration measurement method of the present embodiment, the voltage source 5 includes the first voltage supplier 5a that supplies the first voltage $V_1$ to the first limiting current-type gas sensor element 3a and the second voltage supplier 5b that supplies the second voltage $V_2$ to the second limiting current-type gas sensor element 3b. The second limiting current value $I_2$ (limiting current value of the second limiting current-type gas sensor element 3b) is acquired while the first limiting current value $I_1$ (limiting current value of the first limiting current-type gas sensor element 3a) is acquired. Thus, the time to measure the concentration of the second gas can be shortened.

Embodiment 4

Figure 14:
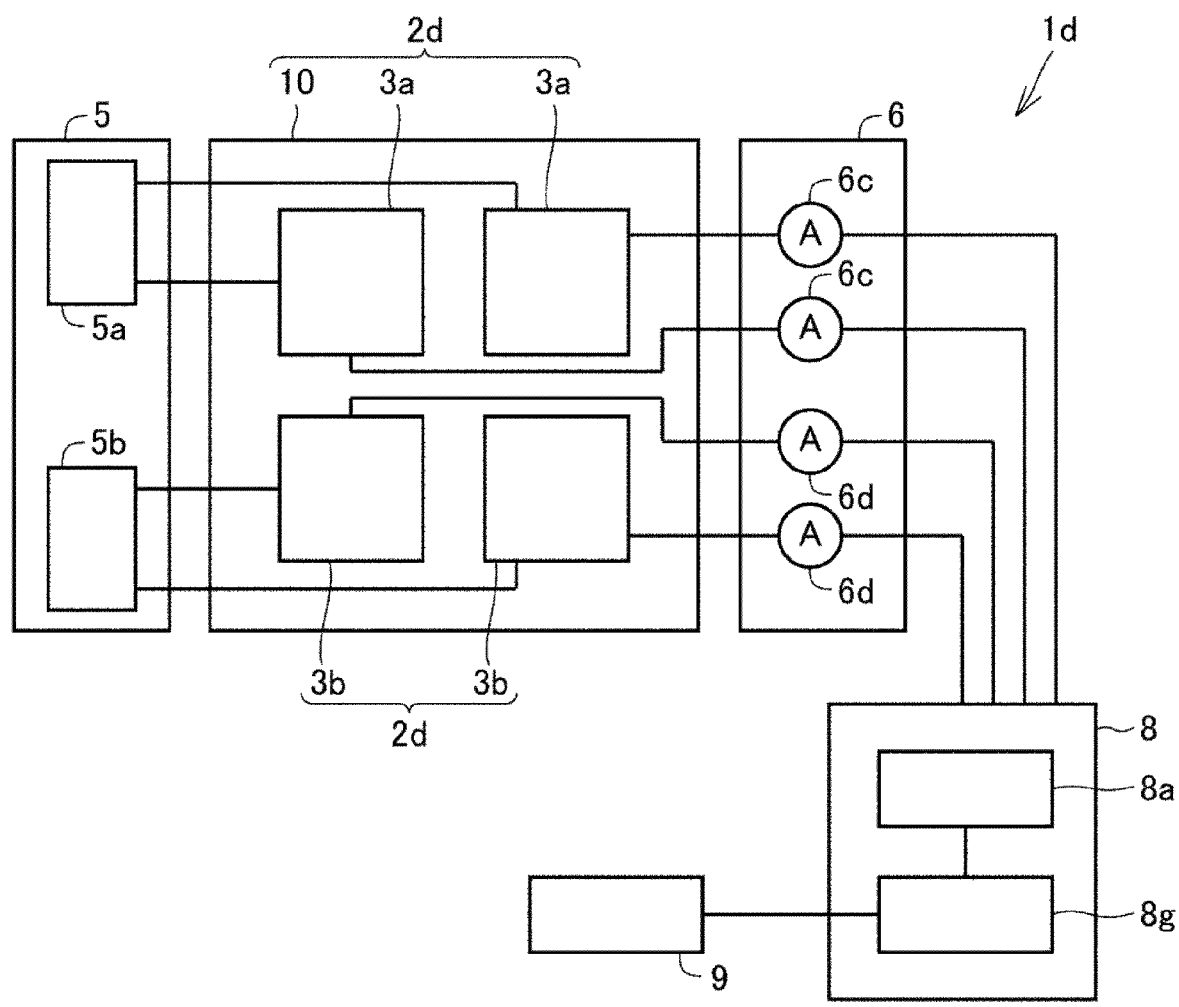
FIG. 14 is a schematic diagram of a gas concentration measurement system of embodiment 4.

A gas concentration measurement system 1d according to embodiment 4 will be described with reference to FIG. 14. The gas concentration measurement system 1d of the present embodiment has a configuration similar to that of the gas concentration measurement system 1 of embodiment 1 but is different mainly in the following points.

In the present embodiment, a limiting current-type gas sensor 2d includes plural first limiting current-type gas sensor elements 3a and plural second limiting current-type gas sensor elements 3b. Each of the plural first limiting current-type gas sensor elements 3a and each of the plural second limiting current-type gas sensor elements 3b have the same configuration as each other. For example, the plural first limiting current-type gas sensor elements 3a and the plural second limiting current-type gas sensor elements 3b each have the same configuration as the limiting current-type gas sensor element 3 of embodiment 1. Concretely, the plural first limiting current-type gas sensor elements 3a and the plural second limiting current-type gas sensor elements 3b each include the solid electrolyte 20, the first electrode 17, the second electrode 27, and the gas introduction path 16. The first electrode 17 is disposed on the solid electrolyte 20. The second electrode 27 is disposed on the solid electrolyte 20. The gas introduction path 16 extends between the gas inlet 35 and the first part 17d opposed to the solid electrolyte 20 in the first electrode 17. The first electrode 17 is the first porous metal electrode. The gas introduction path 16 is formed of the first porous transition metal oxide having the second melting point higher than the first melting point of the first electrode 17. The first porous transition metal oxide is $Ta_2O_5$, $TiO_2$, or $Cr_2O_3$.

The current detector 6 includes plural first current detecting elements 6c corresponding to respective ones of the plural first limiting current-type gas sensor elements 3a and plural second current detecting elements 6d corresponding to respective ones of the plural second limiting current-type gas sensor elements 3b. The plural first current detecting elements 6c acquire first plural limiting current values of the plural first limiting current-type gas sensor elements 3a when the first voltage $V_1$ is applied to the plural first limiting current-type gas sensor elements 3a. The plural second current detecting elements 6d acquire second plural limiting current values of the plural second limiting current-type gas sensor elements 3b when the second voltage $V_2$ is applied to the plural second limiting current-type gas sensor elements 3b.

The difference acquiring section 8a calculates the average value of the difference between the second plural limiting current values and the first plural limiting current values as the difference $\Delta I$ between the second limiting current value $I_2$ and the first limiting current value $I_1$.

In a first example, a first number of plural first limiting current-type gas sensor elements 3a is equal to a second number of plural second limiting current-type gas sensor elements 3b. In this first example, the average value of the difference between the second plural limiting current values and the first plural limiting current values is calculated by calculating the difference between the sum of the second plural limiting current values and the sum of the first plural limiting current values and then dividing this difference by the first number (or second number). The difference between the sum of the second plural limiting current values and the sum of the first plural limiting current values is obtained by subtracting the sum of the first plural limiting current values from the sum of the second plural limiting current values.

In a second example, the average value of the difference between the second plural limiting current values and the first plural limiting current values is calculated by subtracting the average value of the first plural limiting current values from the average value of the second plural limiting current values. The average value of the first plural limiting current values is obtained by dividing the sum of the first plural limiting current values by the first number of plural first limiting current-type gas sensor elements $3a$. The average value of the second plural limiting current values is obtained by dividing the sum of the second plural limiting current values by the second number of plural second limiting current-type gas sensor elements $3b$. In the second example, the first number of plural first limiting current-type gas sensor elements $3a$ may be equal to the second number of plural second limiting current-type gas sensor elements $3b$ or may be different from the second number.

The voltage source 5 may include the first voltage supplier 5a that supplies the first voltage $V_1$ to the plural first limiting current-type gas sensor elements $3a$ and the second voltage supplier 5b that supplies the second voltage $V_2$ to the plural second limiting current-type gas sensor elements $3b$. The second limiting current value $I_2$ (second plural limiting current values) may be acquired while the first limiting current value $I_1$ (first plural limiting current values) is acquired.

Figure 15:
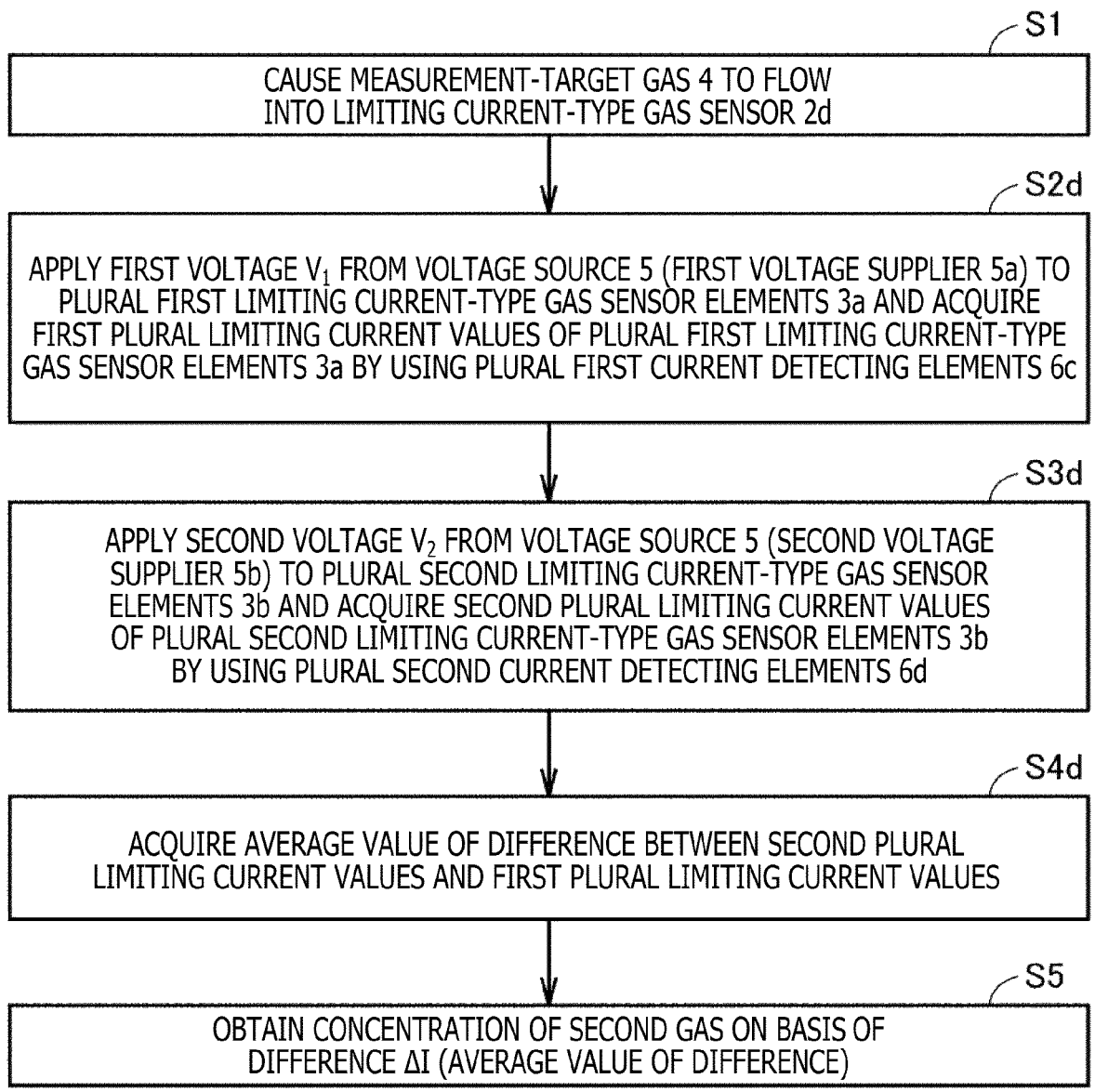
FIG. 15 is a diagram illustrating a flowchart of a gas concentration measurement method of embodiment 4.

A gas concentration measurement method according to embodiment 4 will be described with reference to FIG. 15. The gas concentration measurement method of the present embodiment includes steps similar to those of the gas concentration measurement method of embodiment 1 but is different mainly in the following points.

The gas concentration measurement method of the present embodiment includes applying the first voltage $V_1$ from the voltage source 5 to the plural first limiting current-type gas sensor elements $3a$ and acquiring the first plural limiting current values of the plural first limiting current-type gas sensor elements $3a$ by using the plural first current detecting elements 6c (S2d) as acquiring the first limiting current value $I_1$ in embodiment 1 (S2). The gas concentration measurement method of the present embodiment includes applying the second voltage $V_2$ from the voltage source 5 to the plural second limiting current-type gas sensor element $3b$ and acquiring the second plural limiting current values of the plural second limiting current-type gas sensor elements $3b$ by using the plural second current detecting elements 6d (S3d) as acquiring the second limiting current value $I_2$ in embodiment 1 (S3).

The gas concentration measurement method of the present embodiment includes acquiring the average value of the difference between the second plural limiting current values and the first plural limiting current values (S4b) as acquiring the difference $\Delta I$ between the second limiting current value $I_2$ and the first limiting current value $I_1$ in embodiment 1 (S4). The difference acquiring section 8a calculates the average value of the difference between the second plural limiting current values and the first plural limiting current values. The average value of the difference between the second plural limiting current values and the first plural limiting current values is equivalent to the difference $\Delta I$ between the second limiting current value $I_2$ and the first limiting current value $I_1$.

In the first example, a first number of plural first limiting current-type gas sensor elements $3a$ is equal to a second number of plural second limiting current-type gas sensor elements $3b$. In this first example, the average value of the difference between the second plural limiting current values and the first plural limiting current values is calculated by calculating the difference between the sum of the second plural limiting current values and the sum of the first plural limiting current values and then dividing this difference by the first number (or second number). The difference between the sum of the second plural limiting current values and the sum of the first plural limiting current values is obtained by subtracting the sum of the first plural limiting current values from the sum of the second plural limiting current values.

In the second example, the average value of the difference between the second plural limiting current values and the first plural limiting current values is calculated by subtracting the average value of the first plural limiting current values from the average value of the second plural limiting current values. The average value of the first plural limiting current values is obtained by dividing the sum of the first plural limiting current values by the first number of plural first limiting current-type gas sensor elements $3a$. The average value of the second plural limiting current values is obtained by dividing the sum of the second plural limiting current values by the second number of plural second limiting current-type gas sensor elements $3b$. In the second example, the first number of plural first limiting current-type gas sensor elements $3a$ may be equal to the second number of plural second limiting current-type gas sensor elements $3b$ or may be different from the second number.

In the gas concentration measurement method of the present embodiment, the voltage source 5 may include the first voltage supplier 5a that supplies the first voltage $V_1$ to the plural first limiting current-type gas sensor elements $3a$ and the second voltage supplier 5b that supplies the second voltage $V_2$ to the plural second limiting current-type gas sensor elements $3b$. The second limiting current value $I_2$ (second plural limiting current values) may be acquired while the first limiting current value $I_1$ (first plural limiting current values) is acquired.

The gas concentration measurement system 1d and the gas concentration measurement method of the present embodiment provide the following effects in addition to the effects of the gas concentration measurement system 1 and the gas concentration measurement method of embodiment 1.

In the gas concentration measurement system 1d of the present embodiment, the limiting current-type gas sensor 2d includes the plural first limiting current-type gas sensor elements $3a$ and the plural second limiting current-type gas sensor elements $3b$. The current detector 6 includes the plural first current detecting elements 6c corresponding to respective ones of the plural first limiting current-type gas sensor elements $3a$ and the plural second current detecting elements 6d corresponding to respective ones of the plural second limiting current-type gas sensor elements $3b$. The plural first current detecting elements 6c acquire the first plural limiting current values of the plural first limiting current-type gas sensor elements $3a$ when the first voltage $V_1$ is applied to the plural first limiting current-type gas sensor elements $3a$. The plural second current detecting elements 6d acquire the second plural limiting current values of the plural second limiting current-type gas sensor elements 3b when the second voltage $V_2$ is applied to the plural second limiting current-type gas sensor elements 3b. The difference $\Delta I$ between the second limiting current value $I_2$ and the first limiting current value $I_1$ is the average value of the difference between the second plural limiting current values and the first plural limiting current values.

In the gas concentration measurement system 1d of the present embodiment, the concentration of the second gas is obtained on the basis of the average value of the difference between the second plural limiting current values and the first plural limiting current values. Even when variation exists in the current-voltage characteristic of the plural first limiting current-type gas sensor elements 3a and the plural second limiting current-type gas sensor elements 3b, the concentration of the second gas can be obtained with improved accuracy.

In the gas concentration measurement system 1d of the present embodiment, the voltage source 5 includes the first voltage supplier 5a that supplies the first voltage $V_1$ to the plural first limiting current-type gas sensor elements 3a and the second voltage supplier 5b that supplies the second voltage $V_2$ to the plural second limiting current-type gas sensor elements 3b.

The first voltage supplier 5a and the second voltage supplier 5b make it possible to supply the second voltage $V_2$ to the plural second limiting current-type gas sensor elements 3b while supplying the first voltage $V_1$ to the plural first limiting current-type gas sensor elements 3a. The second limiting current value $I_2$ (second plural limiting current values) can be acquired while the first limiting current value $I_1$ (first plural limiting current values) is acquired. Thus, the time to measure the concentration of the second gas can be shortened.

In the gas concentration measurement method of the present embodiment, the limiting current-type gas sensor 2d includes the plural first limiting current-type gas sensor elements 3a and the plural second limiting current-type gas sensor elements 3b. The current detector 6 includes the plural first current detecting elements 6c corresponding to respective ones of the plural first limiting current-type gas sensor elements 3a and the plural second current detecting elements 6d corresponding to respective ones of the plural second limiting current-type gas sensor elements 3b. Acquiring the first limiting current value $I_1$ (S2) is applying the first voltage $V_1$ to the plural first limiting current-type gas sensor elements 3a and acquiring the first plural limiting current values of the plural first limiting current-type gas sensor elements 3a by using the plural first current detecting elements 6c (S2d). Acquiring the second limiting current value $I_2$ (S3) is applying the second voltage $V_2$ to the plural second limiting current-type gas sensor elements 3b and acquiring the second plural limiting current values of the plural second limiting current-type gas sensor elements 3b by using the plural second current detecting elements 6d (S3d). Acquiring the difference $\Delta I$ between the second limiting current value $I_2$ and the first limiting current value $I_1$ (S4) is acquiring the average value of the difference between the second plural limiting current values and the first plural limiting current values (S4d).

In the gas concentration measurement method of the present embodiment, the concentration of the second gas is obtained on the basis of the average value of the difference between the second plural limiting current values and the first plural limiting current values. Even when variation exists in the current-voltage characteristic of the plural first limiting current-type gas sensor elements 3a and the plural second limiting current-type gas sensor elements 3b, the concentration of the second gas can be obtained with improved accuracy.

In the gas concentration measurement method of the present embodiment, the voltage source 5 includes the first voltage supplier 5a that supplies the first voltage $V_1$ to the plural first limiting current-type gas sensor elements 3a and the second voltage supplier 5b that supplies the second voltage $V_2$ to the plural second limiting current-type gas sensor elements 3b. The second plural limiting current values are acquired while the first plural limiting current values are acquired. Thus, the time to measure the concentration of the second gas can be shortened.

It should be considered that embodiment 1 to embodiment 4 disclosed this time are exemplification in all respects and are not what are restrictive. It is intended that the range of the present disclosure is indicated by not the above explanation but the scope of claims and all changes in meanings and range equivalent to the scope of claims are included therein.

What is claimed is:

1. A gas concentration measurement system, comprising:
   a limiting current-type gas sensor;
   a voltage source connected to the limiting current-type gas sensor;
   a current detector connected to the limiting current-type gas sensor; and
   a gas concentration arithmetic unit connected to the current detector, wherein
   the voltage source is configured to supply a first voltage and a second voltage higher than the first voltage to the limiting current-type gas sensor,
   the first voltage generates a first limiting current corresponding to a first gas in the limiting current-type gas sensor,
   the second voltage generates a second limiting current corresponding to a second gas in the limiting current-type gas sensor,
   the current detector is configured to:
      acquire a first limiting current value of the limiting current-type gas sensor when the first voltage is applied to the limiting current-type gas sensor; and
      acquire a second limiting current value of the limiting current-type gas sensor when the second voltage is applied to the limiting current-type gas sensor,
   the gas concentration arithmetic unit includes circuitry configured to:
      acquire a difference between the second limiting current value and the first limiting current value; and
      obtain a concentration of the second gas on a basis of the difference, a limiting current-type gas sensor element comprising:
      a solid electrolyte,
      a first electrode disposed on the solid electrolyte,
      a second electrode disposed on the solid electrolyte,
      an insulating layer between the second electrode and the solid electrolyte, and
      a gas introduction path is a layer extending between a first part of the first electrode opposed to the solid electrolyte and a gas inlet,
   the insulating layer is disposed on each of:
      an upper surface of the solid electrolyte,
      a side surface of the solid electrolyte,
      a side surface of the first electrode, and
      a side surface of the gas introduction path, and the insulating layer includes an opening in which a second part of the second electrode contacts the solid electrolyte.

2. The gas concentration measurement system according to claim 1, wherein
the limiting current-type gas sensor includes a plurality of limiting current-type gas sensor elements, wherein each of the plurality of limiting current-type gas sensor elements is a duplicate of the limiting current-type gas sensor element,
the current detector includes a plurality of current detecting elements corresponding to respective ones of the plurality of limiting current-type gas sensor elements,
the plurality of current detecting elements is configured to:
acquire a first plurality of limiting current values of the plurality of limiting current-type gas sensor elements when the first voltage is applied to the plurality of limiting current-type gas sensor elements; and
acquire a second plurality of limiting current values of the plurality of limiting current-type gas sensor elements when the second voltage is applied to the plurality of limiting current-type gas sensor elements, and
the circuitry is further configured to determine the difference between an average value of the second plurality of limiting current values and an average value of the first plurality of limiting current values.

3. The gas concentration measurement system according to claim 1, wherein the voltage source is further configured to switch a voltage output to the limiting current-type gas sensor between the first voltage and the second voltage.

4. The gas concentration measurement system according to claim 1, wherein
the limiting current-type gas sensor includes a first limiting current-type gas sensor element and a second limiting current-type gas sensor element, wherein each of the first limiting current-type gas sensor element and the second limiting current-type gas sensor element is a duplicate of the limiting current-type gas sensor element,
the current detector includes a first current detecting element corresponding to the first limiting current-type gas sensor element and a second current detecting element corresponding to the second limiting current-type gas sensor element,
the first current detecting element is configured to acquire a limiting current value of the first limiting current-type gas sensor element when the first voltage is applied to the first limiting current-type gas sensor element as the first limiting current value, and
the second current detecting element is configured to acquire a limiting current value of the second limiting current-type gas sensor element when the second voltage is applied to the second limiting current-type gas sensor element as the second limiting current value.

5. The gas concentration measurement system according to claim 4, wherein the voltage source includes a first voltage supplier configured to supply the first voltage to the first limiting current-type gas sensor element and a second voltage supplier configured to supply the second voltage to the second limiting current-type gas sensor element.

6. The gas concentration measurement system according to claim 1, wherein
the limiting current-type gas sensor includes a plurality of first limiting current-type gas sensor elements and a plurality of second limiting current-type gas sensor elements, wherein each of the plurality of first limiting current-type gas sensor elements and the plurality of second limiting current-type gas sensor elements is a duplicate of the limiting current-type gas sensor element,
the current detector includes a plurality of first current detecting elements corresponding to respective ones of the plurality of first limiting current-type gas sensor elements and a plurality of second current detecting elements corresponding to respective ones of the plurality of second limiting current-type gas sensor elements,
the plurality of first current detecting elements is configured to acquire a first plurality of limiting current values of the plurality of first limiting current-type gas sensor elements when the first voltage is applied to the plurality of first limiting current-type gas sensor elements,
the plurality of second current detecting elements is configured to acquire a second plurality of limiting current values of the plurality of second limiting current-type gas sensor elements when the second voltage is applied to the plurality of second limiting current-type gas sensor elements, and
the circuitry is further configured to determine the difference between an average value of the second plurality of limiting current values and an average value of the first plurality of limiting current values.

7. The gas concentration measurement system according to claim 6, wherein the voltage source includes a first voltage supplier configured to supply the first voltage to the plurality of first limiting current-type gas sensor elements and a second voltage supplier configured to supply the second voltage to the plurality of second limiting current-type gas sensor elements.

8. The gas concentration measurement system according to claim 1, wherein the circuitry includes
an amplifier circuit configured to amplify a first signal corresponding to the first limiting current value and a second signal corresponding to the second limiting current value; and
a difference circuit configured to output the difference between the first signal amplified by the amplifier circuit and the second signal amplified by the amplifier circuit.

9. The gas concentration measurement system according to claim 1, wherein
the first gas is oxygen, and
the second gas is nitrogen oxides ($NO_x$).

10. The gas concentration measurement system according to claim 1, wherein
the first electrode is a first porous metal electrode having a first melting point,
the gas introduction path is formed of a first porous transition metal oxide having a second melting point higher than the first melting point of the first electrode, and
the first porous transition metal oxide is one of $Ta_2O_5$, $TiO_2$, or $Cr_2O_3$.

* * * * *